United States Patent
Richard et al.

(10) Patent No.: US 12,263,184 B2
(45) Date of Patent: Apr. 1, 2025

(54) MATERIALS AND METHODS FOR PRODUCING ARABINOXYLAN COMPOSITIONS

(71) Applicant: Comet Biorefining Inc., London (CA)

(72) Inventors: Andrew Richard, London (CA); Dennis D'Agostino, Waterdown (CA); Ana-Teodora Ivanov-Dragut, Kilworth (CA)

(73) Assignee: Comet Biorefining Inc., London (CA)

( * ) Notice: Subject to any disclaimer, the term of this patent is extended or adjusted under 35 U.S.C. 154(b) by 759 days.

(21) Appl. No.: 17/609,684

(22) PCT Filed: May 8, 2020

(86) PCT No.: PCT/IB2020/054390
§ 371 (c)(1),
(2) Date: Nov. 8, 2021

(87) PCT Pub. No.: WO2020/229977
PCT Pub. Date: Nov. 19, 2020

(65) Prior Publication Data
US 2022/0218735 A1    Jul. 14, 2022

Related U.S. Application Data

(60) Provisional application No. 62/846,291, filed on May 10, 2019.

(51) Int. Cl.
| | |
|---|---|
| A61K 31/717 | (2006.01) |
| A23L 33/00 | (2016.01) |
| A23L 33/24 | (2016.01) |
| A61P 3/02 | (2006.01) |
| C08B 37/00 | (2006.01) |

(52) U.S. Cl.
CPC ............ *A61K 31/717* (2013.01); *A23L 33/24* (2016.08); *A23L 33/30* (2016.08); *A61P 3/02* (2018.01); *C08B 37/0057* (2013.01)

(58) Field of Classification Search
None
See application file for complete search history.

(56) References Cited

U.S. PATENT DOCUMENTS

| | | | |
|---|---|---|---|
| 4,025,389 A | 5/1977 | Poulsen et al. | |
| 5,560,914 A | 10/1996 | Ghoneum et al. | |
| 5,902,782 A | 5/1999 | Hall et al. | |
| 5,967,157 A | 10/1999 | Chatterjee et al. | |
| 6,090,595 A | 7/2000 | Foody et al. | |
| 6,632,448 B2 | 10/2003 | Tanaka et al. | |
| 6,692,578 B2 | 2/2004 | Schmidt et al. | |
| 7,427,643 B2 | 9/2008 | Gatenholm et al. | |
| 7,449,209 B2 | 11/2008 | Dreese et al. | |
| 7,670,678 B2 | 3/2010 | Phan | |
| 7,709,033 B2 | 5/2010 | Kvist et al. | |
| 7,807,419 B2 | 10/2010 | Hennessey et al. | |
| 7,998,713 B2 | 8/2011 | Dunson, Jr. et al. | |
| 8,017,820 B2 | 9/2011 | Foody et al. | |
| 8,022,260 B2 | 9/2011 | O'Connor et al. | |
| 8,148,495 B2 | 4/2012 | Harris et al. | |
| 8,211,483 B2 | 7/2012 | Lee et al. | |
| 8,227,448 B2 | 7/2012 | Van Laere et al. | |
| 8,318,458 B2 | 11/2012 | Harris et al. | |
| 8,460,898 B2 | 6/2013 | Diner et al. | |
| 8,465,788 B2 | 6/2013 | Ekhart et al. | |
| 8,623,402 B2 | 1/2014 | Delcour | |
| 8,658,405 B2 | 2/2014 | Johal et al. | |
| 8,685,690 B2 | 4/2014 | Yang et al. | |
| 8,741,376 B2 | 6/2014 | Broekaert et al. | |
| 8,778,639 B1 | 7/2014 | Spodsberg | |
| 8,809,033 B2 | 8/2014 | Sweeney et al. | |
| 8,815,561 B2 | 8/2014 | Liu et al. | |
| 8,877,474 B2 | 11/2014 | Yang et al. | |
| 8,894,771 B2 | 11/2014 | Floyd et al. | |
| 8,927,038 B2 | 1/2015 | Broekaert et al. | |
| 8,962,288 B2 | 2/2015 | Quinlan et al. | |
| 9,061,046 B2 | 6/2015 | Broekaert et al. | |
| 9,080,165 B2 | 7/2015 | Fidantsef et al. | |
| 9,109,213 B2 | 8/2015 | Schooneveld-Bergmans et al. | |

(Continued)

FOREIGN PATENT DOCUMENTS

| | | |
|---|---|---|
| CA | 1175820 | 10/1984 |
| CA | 2615904 | 2/1994 |

(Continued)

OTHER PUBLICATIONS

Mathew, Sindhu, Eva Nordberg Karlsson, and Patrick Adlercreutz. "Extraction of soluble arabinoxylan from enzymatically pretreated wheat bran and production of short xylo-oligosaccharides and arabinoxylo-oligosaccharides from arabinoxylan by glycoside hydrolase family 10 and 11 endoxylanases." Journal of biotechnol.*

Damay, Jérémie, et al. "Steam explosion of sweet sorghum stems: optimisation of the production of sugars by response surface methodology combined with the severity factor." Industrial Crops and Products 111 (2018): 482-493.*

Peng, Feng, et al. "Fractional purification and bioconversion of hemicelluloses." Biotechnology advances 30.4 (2012): 879-903.*

Extended European Search Report in European Appln No. 20805657.2, dated Dec. 15, 2022, 8 pages.

Alkasrawi et al, "The effect of Tween-20 on simultaneous saccharification and fermentation of softwood to Ethanol", Enzyme and Microbial Technology, 2003, 33:71-78.

Belafi-Bako et al., "Continuous enzymatic cellulose hydrolysis in a tubular membrane bioreactor," Enzyme and Microbial Technology, 38(1-2):155-161, Jan. 2006.

(Continued)

*Primary Examiner* — Patrick T Lewis
(74) *Attorney, Agent, or Firm* — Fish & Richardson P.C.

(57) ABSTRACT

This document provides compositions containing arabinoxylan, methods for making compositions containing arabinoxylan, and methods for using compositions containing arabinoxylan as, for example, a food ingredient, dietary supplement ingredient, or pharmaceutical ingredient. In particular, the document discloses the use of lignocellulosic biomass with water at temperatures and pressures to provide the disclosed products.

21 Claims, 1 Drawing Sheet

(56) References Cited

U.S. PATENT DOCUMENTS

| | | |
|---|---|---|
| 9,121,013 B2 | 9/2015 | Schooneveld-Bergmans et al. |
| 9,150,936 B2 | 10/2015 | Dottori et al. |
| 9,163,223 B2 | 10/2015 | Schooneveld-Bergmans et al. |
| 9,175,050 B2 | 11/2015 | Schooneveld-Bergmans et al. |
| 9,175,277 B2 | 11/2015 | McBrayer et al. |
| 9,193,982 B2 | 11/2015 | Sjoede et al. |
| 9,200,302 B2 | 12/2015 | Cotti Comettini et al. |
| 9,260,704 B2 | 2/2016 | Schooneveld-Bergmans et al. |
| 9,303,074 B2 | 4/2016 | Schnorr et al. |
| 9,353,363 B2 | 5/2016 | Lange et al. |
| 9,365,843 B2 | 6/2016 | Zhang et al. |
| 9,370,193 B2 | 6/2016 | Sorensen et al. |
| 9,410,136 B2 | 8/2016 | Schnorr et al. |
| 9,428,772 B2 | 8/2016 | Hamrick |
| 9,434,788 B2 | 9/2016 | Yadav et al. |
| 9,441,214 B2 | 9/2016 | Schooneveld-Bergmans et al. |
| 9,506,049 B2 | 11/2016 | Tang et al. |
| 9,506,098 B2 | 11/2016 | Cotti Comettini et al. |
| 9,624,481 B2 | 4/2017 | Liu et al. |
| 9,677,060 B2 | 6/2017 | Johansen et al. |
| 9,689,011 B2 | 6/2017 | Ellegård et al. |
| 9,695,433 B2 | 7/2017 | Zhang et al. |
| 9,738,881 B2 | 8/2017 | Los et al. |
| 9,752,168 B2 | 9/2017 | Quinlan et al. |
| 9,752,169 B2 | 9/2017 | Cotti Comettini et al. |
| 9,765,373 B2 | 9/2017 | Schnorr et al. |
| 9,771,568 B2 | 9/2017 | Liu et al. |
| 9,783,860 B2 | 10/2017 | Floyd et al. |
| 9,790,530 B2 | 10/2017 | Shaghasi et al. |
| 9,795,628 B2 | 10/2017 | Hageman |
| 9,797,021 B2 | 10/2017 | Floyd et al. |
| 9,848,626 B2 | 12/2017 | Shen et al. |
| 9,879,294 B2 | 1/2018 | Huang et al. |
| 9,896,707 B2 | 2/2018 | Thompson et al. |
| 9,932,414 B2 | 4/2018 | Quinlan et al. |
| 9,957,491 B2 | 5/2018 | Zhang et al. |
| 9,963,725 B2 | 5/2018 | Lali et al. |
| 9,994,833 B2 | 6/2018 | Liu et al. |
| 10,041,136 B2 | 8/2018 | St. John et al. |
| 10,131,715 B2 | 11/2018 | Hepworth et al. |
| 10,174,351 B2 | 1/2019 | Smits et al. |
| 10,190,103 B2 | 1/2019 | Börjesson et al. |
| 10,207,197 B2 | 2/2019 | Mitchell |
| 10,246,522 B2 | 4/2019 | Hepworth et al. |
| 10,308,921 B2 | 6/2019 | Tang et al. |
| 10,633,461 B2 | 4/2020 | Richard et al. |
| 11,406,120 B2 | 8/2022 | Falck |
| 11,525,016 B2 | 12/2022 | Richard et al. |
| 2002/0037331 A1 | 3/2002 | Hwang et al. |
| 2005/0209122 A1 | 9/2005 | Jorgensen et al. |
| 2008/0227166 A1 | 9/2008 | Allain et al. |
| 2009/0056889 A1 | 3/2009 | Ren et al. |
| 2009/0062232 A1 | 3/2009 | Fujikawa et al. |
| 2010/0035302 A1 | 2/2010 | Broekaert et al. |
| 2010/0298611 A1 | 11/2010 | Parekh et al. |
| 2011/0020498 A1 | 1/2011 | Broekaert et al. |
| 2011/0020873 A1 | 1/2011 | Ren et al. |
| 2011/0111456 A1 | 5/2011 | Medoff |
| 2011/0159554 A1 | 6/2011 | Takahashi et al. |
| 2011/0250645 A1 | 10/2011 | Schiffino et al. |
| 2011/0263004 A1 | 10/2011 | Illvesniemi et al. |
| 2011/0300586 A1 | 12/2011 | Liu et al. |
| 2012/0015902 A1 | 1/2012 | Broekaert et al. |
| 2012/0111514 A1 | 5/2012 | Dottori et al. |
| 2012/0230955 A1 | 9/2012 | Ekhart et al. |
| 2012/0240921 A1 | 9/2012 | Fukuoka et al. |
| 2013/0004994 A1 | 1/2013 | Hanakawa |
| 2013/0005952 A1 | 1/2013 | Belanger et al. |
| 2013/0029406 A1 | 1/2013 | Dottori et al. |
| 2013/0052713 A1 | 2/2013 | Yang et al. |
| 2013/0059345 A1 | 3/2013 | Kurihara et al. |
| 2013/0244293 A1 | 9/2013 | Balan et al. |
| 2013/0261340 A1 | 10/2013 | Medoff |
| 2014/0038244 A1 | 2/2014 | Chesonis et al. |
| 2014/0093918 A1 | 4/2014 | Zhang et al. |
| 2014/0106418 A1 | 4/2014 | Parekh et al. |
| 2015/0307952 A1 | 10/2015 | Saville |
| 2015/0368372 A1 | 12/2015 | Yadav et al. |
| 2016/0249662 A1 | 9/2016 | Medoff |
| 2017/0369517 A1 | 12/2017 | Shekiro, III et al. |
| 2018/0119188 A1 | 5/2018 | Richard et al. |
| 2019/0345265 A1 | 11/2019 | Richard et al. |
| 2020/0216574 A1 | 7/2020 | Richard et al. |
| 2023/0167202 A1 | 6/2023 | Richard et al. |

FOREIGN PATENT DOCUMENTS

| | | |
|---|---|---|
| CA | 2179970 | 12/1996 |
| CA | 2189899 | 5/1997 |
| CA | 2240035 | 12/1998 |
| CA | 2282094 | 4/2000 |
| CA | 2368872 | 10/2000 |
| CA | 2373936 | 1/2001 |
| CA | 2400336 | 8/2001 |
| CA | 2418726 | 2/2002 |
| CA | 2420064 | 2/2002 |
| CA | 2477196 | 8/2003 |
| CA | 2583256 | 3/2006 |
| CA | 2580226 | 4/2006 |
| CA | 2580228 | 4/2006 |
| CA | 2535246 | 8/2006 |
| CA | 2603645 | 10/2006 |
| CA | 2831082 | 1/2007 |
| CA | 2655035 | 12/2007 |
| CA | 2595484 | 2/2008 |
| CA | 2565433 | 4/2008 |
| CA | 2576317 | 7/2008 |
| CA | 2674534 | 7/2008 |
| CA | 2684007 | 10/2008 |
| CA | 2685177 | 11/2008 |
| CA | 2691524 | 12/2008 |
| CA | 2694245 | 1/2009 |
| CA | 2694875 | 2/2009 |
| CA | 2697962 | 2/2009 |
| CA | 2698641 | 3/2009 |
| CA | 2701862 | 4/2009 |
| CA | 2701949 | 4/2009 |
| CA | 2703085 | 5/2009 |
| CA | 2720177 | 10/2009 |
| CA | 2731983 | 2/2010 |
| CA | 2731350 | 3/2010 |
| CA | 2739451 | 4/2010 |
| CA | 2739704 | 5/2010 |
| CA | 2739709 | 5/2010 |
| CA | 2746783 | 6/2010 |
| CA | 2738886 | 7/2010 |
| CA | 2745508 | 7/2010 |
| CA | 2715458 | 10/2010 |
| CA | 2714946 | 12/2010 |
| CA | 2763588 | 12/2010 |
| CA | 2673134 | 1/2011 |
| CA | 2714937 | 1/2011 |
| CA | 2767290 | 1/2011 |
| CA | 2789199 | 1/2011 |
| CA | 2772112 | 3/2011 |
| CA | 2772115 | 3/2011 |
| CA | 2775355 | 4/2011 |
| CA | 2775656 | 4/2011 |
| CA | 2783794 | 6/2011 |
| CA | 2784105 | 6/2011 |
| CA | 2783201 | 7/2011 |
| CA | 2786949 | 8/2011 |
| CA | 2786951 | 8/2011 |
| CA | 2788548 | 8/2011 |
| CA | 2695823 | 9/2011 |
| CA | 2795503 | 9/2011 |
| CA | 2800996 | 12/2011 |
| CA | 2804662 | 1/2012 |
| CA | 2806130 | 2/2012 |
| CA | 2806132 | 2/2012 |
| CA | 2802221 | 3/2012 |
| CA | 2809519 | 3/2012 |
| CA | 2810455 | 4/2012 |
| CA | 2811681 | 4/2012 |

(56) References Cited

FOREIGN PATENT DOCUMENTS

| | | |
|---|---|---|
| CA | 2818759 | 5/2012 |
| CA | 2818175 | 6/2012 |
| CA | 2693125 | 8/2012 |
| CA | 2434144 | 12/2012 |
| CA | 2838560 | 1/2013 |
| CA | 2842781 | 1/2013 |
| CA | 2860704 | 7/2013 |
| CA | 2873106 | 11/2013 |
| CA | 2820210 | 12/2013 |
| CA | 2569856 | 9/2014 |
| CA | 2900759 | 9/2014 |
| CA | 2746008 | 5/2016 |
| CA | 2733551 | 6/2016 |
| CA | 2982187 | 10/2016 |
| CA | 2756541 | 8/2019 |
| CN | 103896992 | 7/2014 |
| CN | 104136466 | 11/2014 |
| CN | 108291244 | 7/2018 |
| EP | 1758470 | 7/2008 |
| EP | 1675481 | 11/2008 |
| EP | 2270237 | 1/2011 |
| EP | 2179048 | 2/2012 |
| EP | 2414532 | 2/2012 |
| EP | 2355670 | 3/2013 |
| EP | 2265127 | 10/2013 |
| EP | 2313514 | 11/2016 |
| EP | 2621503 | 11/2017 |
| EP | 2323669 | 7/2018 |
| EP | 2117322 | 10/2018 |
| EP | 2648540 | 10/2018 |
| EP | 3157340 | 12/2018 |
| EP | 2582820 | 4/2019 |
| JP | H05253000 | 10/1993 |
| JP | H05-317075 | 12/1993 |
| JP | H06-217761 | 8/1994 |
| JP | 2001-145498 | 5/2001 |
| JP | 2004-182609 | 7/2004 |
| JP | 2004-210666 | 7/2004 |
| JP | 2006-075067 | 3/2006 |
| JP | 2007-269659 | 10/2007 |
| JP | 4039550 | 1/2008 |
| JP | 2017-530701 | 10/2017 |
| JP | 2018-512178 | 5/2018 |
| WO | WO 1994/029424 | 12/1994 |
| WO | WO 1995/020065 | 7/1995 |
| WO | WO 2001/030855 | 5/2001 |
| WO | WO 2001/067891 | 9/2001 |
| WO | WO 2006/027529 | 3/2006 |
| WO | WO 2010/071805 | 6/2010 |
| WO | WO 2011/046816 | 4/2011 |
| WO | WO 2011/157968 | 12/2011 |
| WO | WO 2012/040003 | 3/2013 |
| WO | WO 2013/040702 | 3/2013 |
| WO | WO 2013/071883 | 5/2013 |
| WO | WO 2013/101650 | 7/2013 |
| WO | WO 2013/117823 | 8/2013 |
| WO | WO 2013/131015 | 9/2013 |
| WO | WO 2013/163571 | 10/2013 |
| WO | WO 2013/164234 | 11/2013 |
| WO | WO 2013/171100 | 11/2013 |
| WO | WO 2014/026154 | 2/2014 |
| WO | WO 2014/031667 | 2/2014 |
| WO | WO 2014/110223 | 7/2014 |
| WO | WO 2014/119990 | 8/2014 |
| WO | WO 2014/144588 | 9/2014 |
| WO | WO 2014/147393 | 9/2014 |
| WO | WO 2015/016930 | 2/2015 |
| WO | WO 2015/040159 | 3/2015 |
| WO | WO 2015/050881 | 4/2015 |
| WO | WO 2015/063549 | 5/2015 |
| WO | WO 2015/086782 | 6/2015 |
| WO | WO 2015/086783 | 6/2015 |
| WO | WO 2015/101693 | 7/2015 |
| WO | WO 2015/104460 | 7/2015 |
| WO | WO 2015/107413 | 7/2015 |
| WO | WO 2015/176173 | 11/2015 |
| WO | WO 2016/005519 | 1/2016 |
| WO | WO 2016/045569 | 3/2016 |
| WO | WO 2016/161515 | 10/2016 |
| WO | WO 2017/044039 | 3/2017 |
| WO | WO 2017/147163 | 8/2017 |
| WO | WO 2019217844 | 11/2019 |

OTHER PUBLICATIONS

Bensah and Mensah, "Chemical Pretreatment Methods for the Production of Cellulosic Ethanol: Technologies and Innovations," International Journal of Chemical Engineering, 2013, 21 pages.

Brethauer et al, "The effect of bovine serum albumin on batch and continuous enzymatic cellulose hydrolysis mixed by stirring or shaking", Bioresource Technology, 2011, 102:6295-6298.

Carrasco et al., "Steam pretreatment and fermentation of the straw material Paja brava using simultaneous saccharification and co-fermentation," J. Biosci. Bioengineering, Oct. 18, 2010, 111(2):167-174.

Correia et al., "Structure and Function of an Arabinoxylan-specific Xylanase," J. Biol. Chemistry, Jun. 24, 2011, 286(25):22510-22520.

Dekker and Wallis, "Enzymic Saccharification of Sugarcane Bagasse Pretreated by Autohydrolysis—Steam Explosion" Biotechnology and Bioengineering, 1983, 25:3027-3048.

Ding et al., "Enzymatic conversion of cellulosic materials in a continuous stirred take reactor with an ultrafiltration membrane," Food for Health in the Pacific Rim: 3rd International Conference of Food Science and Technology. Trumbull, Connecticut, USA: Food & Nutrition Press, Inc., pp. 433-445, Dec. 2004.

Fang et al., Polymer Degradation and Stability, 1999, 66, p. 423-432. (Year: 1999).

Ghose et al., "A model for continuous enzymatic saccharification of cellulose with simultaneous removal of glucose syrup," Biotechnol. Bioeng., 12(6):921-946, Nov. 1970.

Gonçalves et al., "Functional characterization and synergic action of fungal xylanase and arabinofuranosidase for production of xylooligosaccharides," Bioresour. Technology, May 2012, 119:293-299.

Harris et al, "Two-Stage, Dilute Sulfuric Acid Hydrolysis of Hardwood for Ethanol Production" Energy Research, Development, and Application, Forest Products Laboratory, Forest Service, USDA, Madison, Wisconsin 53705, 1984, 20 pages.

Hodge et al., "Model-based fed-batch for high-solids enzymatic cellulose hydrolysis," Appl. Biochem. Biotechnol., 152(1):88-107, Jan. 2009.

Hooshmand, "Purification and Characterisation of Xylooligosaccharides (XOS) From Wheat-Based Dried Distillers Grains With Solubles," Thesis for the degree of Master of Chemistry, Lund University, 2012, 30 pages.

Kaya et al, "Influence of surfactants on the enzymatic hydrolysis of xylan and cellulose", Tappi Journal, 1995, 78:(10):150-157.

Kyung et al., "Effects of xylooligosaccharide-sugar mixture on glycemic index (GI) and blood glucose response in healthy adults," J. Nutr. Health, Aug. 2014, 47(4):229-235 (with English Abstract).

Mandelli et al., "Simultaneous production of xylooligosaccharides and antioxidant compounds from sugarcane bagasse via enzymatic hydrolysis," Ind. Crops Products, Jan. 2014, 52:770-775.

Mandels et al., "The use of adsorbed cellulase in the continuous conversion of cellulose to glucose," J. Polymer Sci., 36(1):445-459, 1971.

McCleary et al., "Hydrolysis of wheat flour arabinoxylan, acid-debranched wheat flour arabinoxylan and arabino-xylo-oligosaccharides by β-xylanase, α-L-arabinofuranosidase and β-xylosidase," Carbohydr. Research, Apr. 2015, 407:79-96.

Perez and Samain, "Structure and Engineering of Cellulose" Advances in Carbohydrate Chemistry and Biochemistry, 64:22-116, Jan. 2010.

Sun et al., "Structural Characterization of Hemicelluloses from Bamboo Culms," Cellulose Chemistry and Technology, 2012, 46(3-4):165-76.

Tanaka et al., "Removal of lignin and reuse of cellulases for continuous saccharification of lignocelluloses," Biotechnol. Bioeng., 32(7):897-902, Sep. 1988.

(56) References Cited

OTHER PUBLICATIONS

Tjerneld et al, "Enzymatic Hydrolysis of Cellulose in Aqueous Two-Phase Systems. II. Semicontinuous Conversion of a Model Substrate, Solka Floe BW 200", Biotechnology and Bioengineering, 1985, 27:1044-1050.
Tjerneld et al., "Enzymatic hydrolysis of cellulose in aqueous two-phase systems. I. partition of cellulases from Trichoderma reesei", Biotechnology and Bioengineering, 27(7):1036-43, Jul. 1985.
Tu et al, "The potential of enzyme recycling during the hydrolysis of a mixed softwood feedstock", Bioresource Technology, 2009, 100:6407-6415.
Wang, "Cellulose Fiber Dissolution in Sodium Hydroxide Solution at Low Temperature: Dissolution Kinetics and Solubility Improvement," Georgia Institute of Technology, 2008, 148 pages.
Yang et al., "Aqueous extraction of corncob xylan and production of xylooligosaccharides," LWT-Food Science and Technology, 38(6):677-82, Sep. 2005.
U.S. Appl. No. 16/409,335, filed May 10, 2019, Andrew Richard, now U.S. Pat. No. 10,633,461.
U.S. Appl. No. 16/783,622, filed Feb. 6, 2020, Andrew Richard, Published as U.S. Patent Application Publication No. 2020/0216574.
Zheng et al., "[Functional Food]," Sep. 1999, vol. 2, China Light Industry Press, Chapter 2, Section 1, Part 1, pp. 56-57 (with Machine Translation), 12 pages.
[No Author], "AOAC Official Method 2011.25: Insoluble, Soluble, and Total Dietary Fiber in Foods," AOAC International, 2012, 10 pages.
Akpinar et al., "Enzymatic Processing and Antioxidant Activity of Agricultural Waste Autohydrolysis Liquors," BioResources, 2010, 5(2):699-711.
Cheng et al., "Separation, Purification and Characterization of Corn Stover Hemicelluloses," Cellulose Che. Technology, May 2017, 51(3-4):215-222.
Cloetens et al., "Tolerance of arabinoxylan-oligosaccharides and their prebiotic activity in healthy subjects: a randomised, placebo-controlled cross-over study," Br. J. Nutrition, Mar. 2010, 103(5):703-713.
Egüés et al., "Effect of alkaline and autohydrolysis processes on the purity of obtained hemicelluloses from corn stalks," Bioresour. Technology, Jan. 2012, 103(1):239-248.
Francois et al., "Effects of a wheat bran extract containing arabinoxylan oligosaccharides on gastrointestinal health parameters in healthy adult human volunteers: a double-blind, randomised, placebo-controlled, cross-over trial," Br. J. Nutrition, Dec. 28, 2012, 108(12):2229-2242.
Francois et al., "Tolerance and the effect of high doses of wheat bran extract, containing arabinoxylan-oligosaccharides, and oligofructose on faecal output: a double-blind, randomised, placebo-controlled, cross-over trial," J. Nutr. Science, Oct. 20, 2014, 3:e49, 12 pages.
Horii et al., "Hypocholesterolemic Activity of Desalted Miso in Rats Fed an Atherogenic Diet," Nippon Shokuhin Kogyo Gakkaishi, 1990, 37(2):148-153.
Lu et al., "Arabinoxylan fiber, a byproduct of wheat flour processing, reduces the postprandial glucose response in normoglycemic subjects," Am. J. Clin. Nutrition, May 2000, 71(5):1123-1128.
Magaletta et al., "In vitro method for predicting glycemic index of foods using simulated digestion and an artificial neural network" Cereal Chemistry, Jul./Aug. 2010, 87(4):363-369.
Malunga et al., "Antioxidant Capacity of Water-Extractable Arabinoxylan from Commercial Barley, Wheat, and Wheat Fractions," Cereal Chemistry, Jan./Feb. 2015, 92(1):29-36.
Nour et al., "HPLC Determination of Phenolic Acids, Flavonoids and Juglone in Walnut Leaves," J. Chromatogr. Science, Oct. 2013, 51(9):883-890.
PCT International Preliminary Report on Patentability in International Appln. No. PCT/IB2020/054390, dated Nov. 16, 2021, 5 pages.
PCT International Search Report and Written Opinion in International Appln. No. PCT/IB2020/054390, dated Jul. 24, 2020, 9 pages.
Schutte et al., "Nutritional implications of L-arabinose in pigs," Br. J. Nutrition, 1992, 68:195-207.
Sluiter et al., "Determination of Sugars, Byproducts, and Degradation Products in Liquid Fraction Process Samples," Technical Report NREL/TP-510-42623, U.S. Department of Energy: National Renewable Energy Laboratory, Jan. 2008, 14 pages.
Sun et al., "Physico-chemical and structural characterization of hemicelluloses from wheat straw by alkaline peroxide extraction," Polymer, Mar. 2000, 41(7):2647-2656.
[Production Technology and Product Quality Control Standards for Sugar and Sugar Products], Ding Jihua (ed)., Ethnic Publishing House, Aug. 2003, pp. 89-93 (with Machine Translation).
Bataillon et al., "Extraction and purification of arabinoxylan from destarched wheat bran in a pilot scale," Industrial Crops and Products, Mar. 1998, 8(1):37-43.
Sanchez-Bastardo et al., "Extraction of arabinoxylans from wheat bran using hydrothermal processes assisted by heterogeneous catalysts," Carbohydr. Polym., Mar. 2017, 160:143-152.
Vegas et al., "Evaluation of ultra- and nanofiltration for refining soluble products from rice husk xylan," Bioresour. Technol., Sep. 2008, 99(13):5341-5351.
Yuan et al., "Pilot-plant production of xylo-oligosaccharides from corncob by steaming, enzymatic hydrolysis and nanofiltration," J. Chem. Technol. Biotechnol., Oct. 2004, 79(10):1073-1079.
Zhao et al., "Effect of activated charcoal treatment of alkaline hydrolysates from sugarcane bagasse on purification of p-coumaric acid," Chem. Eng. Res. Des., Oct. 2011, 89(10):2176-2181.

* cited by examiner

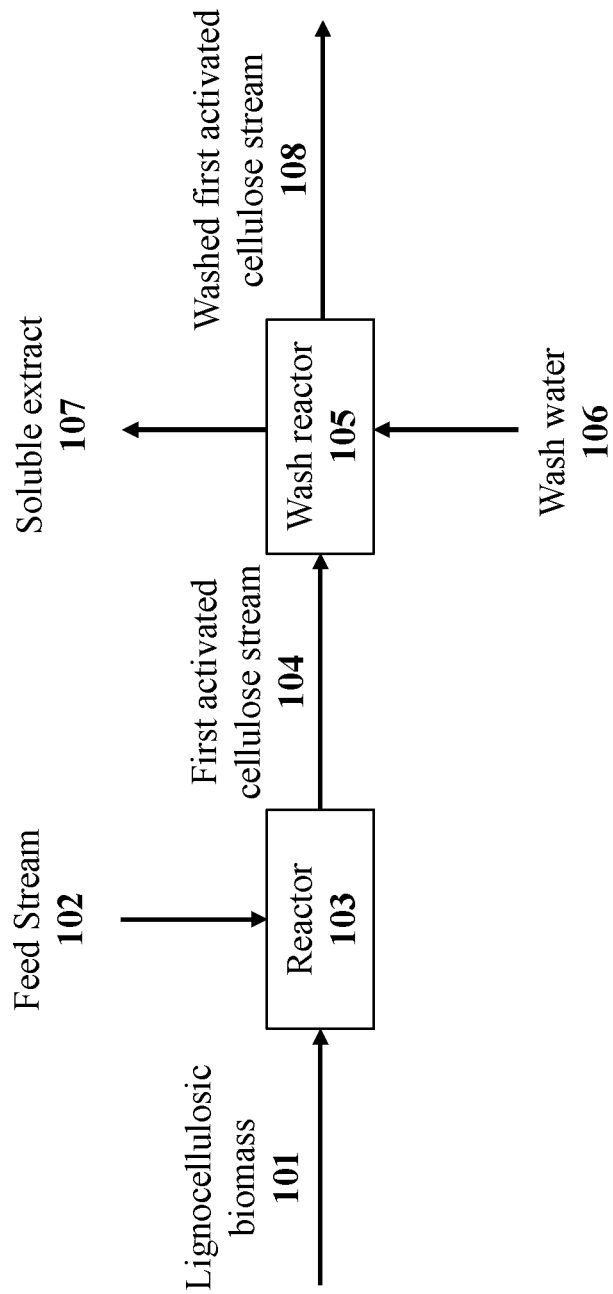

MATERIALS AND METHODS FOR PRODUCING ARABINOXYLAN COMPOSITIONS

CROSS-REFERENCE TO RELATED APPLICATIONS

This application is a National State Application under 35 U.S.C. § 371 of International Application No. PCT/IB2020/054390, filed May 8, 2020, which claims priority to U.S. Application Ser. No. 62/846,291, filed on May 10, 2019, each of which is incorporated by reference herein in its entirety.

TECHNICAL FIELD

This document relates to compositions containing arabinoxylan, methods for making compositions containing arabinoxylan, and methods for using compositions containing arabinoxylan as, for example, a food ingredient or a dietary supplement.

BACKGROUND

Fiber can be found in plant-based foods and is a common dietary supplement. Fiber can include prebiotic fiber (sometimes called soluble fiber) and/or insoluble fiber.

Prebiotic fiber is a non-digestible part of foods that goes through the small intestine undigested and is fermented when it reaches the colon. The fermentation process can feed beneficial bacteria colonies in the digestive tract and may help to increase the number of desirable bacteria in a digestive system, which may reduce the risk of certain diseases and improve overall health. Non-limiting examples of prebiotic fiber include arabinoxylan, inulin, pectin, alginic acids, raffinose, and xylose.

Fiber compositions that are derived from plant sources can be a source of prebiotic fiber. According to the Dietary Guidelines produced by the United States Department of Agriculture, the recommended daily intake of fiber on a 2,000 calorie diet is about 28 g. Fiber compositions also can include naturally occurring sweetening agents or added sweetening agents. Fiber compositions can be used to provide bulk in calorie reduced products, as long chain fibers are not readily digested and pass through the gut. Soluble fiber in the diet can improve digestion by drawing water into the intestines. Fiber compositions also can create a feeling of fullness and prevent blood glucose and insulin spikes, thereby reducing food cravings and reducing or preventing intake of inappropriate foods or inappropriate amounts of foods.

SUMMARY

This document provides compositions containing arabinoxylan, methods for making compositions containing arabinoxylan, and methods for using compositions containing arabinoxylan as, for example, a food ingredient, dietary supplement ingredient, or pharmaceutical ingredient. For example, this document provides compositions (e.g., arabinoxylan compositions) containing predominately arabinoxylan (e.g., greater than 88% percent arabinoxylan by dry weight) that has a molecular weight ($M_w$) of about 5500 to about 6000 Da. In some cases, a composition (e.g., arabinoxylan compositions) provided herein can have a content of carbohydrate polymers that are not arabinoxylan less than about 1% by dry weight, and a polyphenol content of about 1% to about 3% by dry weight. Typically, plants such as wheat and corn contain arabinoxylan molecules with molecular weights ($M_w$) of at least about 100 kDa and with covalently attached polyphenols, and extracting this arabinoxylan can result in compositions containing carbohydrate polymers other than arabinoxylan from about 7% to about 30%, a sugar monomer content of about 0.5% to about 7.5%, a protein content of about 0.5% to about 25%, and an ash content of about 0.1% to about 3%. As described herein, plant material can be processed as described herein to produce compositions (e.g., arabinoxylan compositions) that (a) contain predominately arabinoxylan (e.g., greater than 88 percent arabinoxylan by dry weight) that has a molecular weight ($M_w$) of 5500-6000 Da and (b) have other desirable structural and/or functional characteristics such as a content of carbohydrate polymers that are not arabinoxylan less than about 1%, a polyphenol content of about 1% to about 12% by dry weight, a content of ferulic acid units (e.g., as components of polyphenols, free units, or a combination thereof) of 0.0005% to about 0.005%, a content of gallic acid units (e.g., as components of polyphenols, free units, or a combination thereof) of about 0.005% to about 0.02%, a content of epigallocatechin-3-gallate units, and/or a color (e.g., when in powder form) of light brown. Having the ability to produce large amounts of the compositions (e.g., arabinoxylan compositions) described herein using the methods and materials described herein can allow manufacturers to provide customers with a rich source of arabinoxylan having desirable structural and functional characteristics for use in, for example, food products, dietary supplements, and/or pharmaceutical compositions.

In one aspect, provided herein is a composition including about 88% to about 99% by dry weight of arabinoxylan, about 4% to about 12% by dry weight of carbohydrate polymers other than arabinoxylan, sugar monomers, protein, and ash, and about 1% to about 12% by dry weight of one or more polyphenols.

Implementations can include one or more of the following features. The composition can include about 88% to about 90% by dry weight of arabinoxylan. The composition can include about 90% to about 99% by dry weight of arabinoxylan. The composition can include about 90% to about 95% by dry weight of arabinoxylan. The composition can include about 91% to about 93% by dry weight of arabinoxylan. The composition can include about 6% to about 10% by dry weight of carbohydrate polymers other than arabinoxylan, sugar monomers, protein, ash, or a combination thereof. The composition can include about 5% to about 7% by dry weight of carbohydrate polymers other than arabinoxylan, sugar monomers, protein, ash, or a combination thereof. The composition can include about 8% to about 10% by dry weight of carbohydrate polymers other than arabinoxylan, sugar monomers, protein, ash, or a combination thereof. The composition can include about 2% to about 5% by dry weight of one or more polyphenols. The composition can include about 5% to about 10% by dry weight of one or more polyphenols. The composition can include about 1% to about 3% by dry weight of one or more polyphenols. The composition can include about 1% to about 2% by dry weight of one or more polyphenols. The arabinoxylan can include about 5% to about 25% by dry weight of arabinose units. The arabinoxylan can include about 5% to about 15% by dry weight of arabinose units. The arabinoxylan can include about 10% to about 20% by dry weight of arabinose units. The arabinoxylan can include about 15% to about 25% by dry weight of arabinose units. The arabinoxylan can include about 5% to about 7% by dry weight of arabinose units. The arabinoxylan can include about 18% to about 20% by dry weight of arabinose units. The arabinoxylan can include about 60% to about 85% by dry weight of xylose units. The arabinoxylan can include about 60% to about 70% by dry weight of xylose units. The arabinoxylan can include about 70% to about 80% by dry weight of xylose units. The arabinoxylan can include about 75% to about 85% by dry weight of xylose units. The arabinoxylan can include about 62% to about 66% by dry weight of xylo se units. The arabinoxylan can include about 78% to about 82% by dry weight of xylo se units. The arabinoxylan can include about 8% to about 15% by dry weight of glucose units. The arabinoxylan can include about 10% to about 15% by dry weight of glucose units. The arabinoxylan can include about 9% to about 11% by dry weight of glucose units. The arabinoxylan can include about 12% to about 14% by dry weight of glucose units. The arabinoxylan can include about 2% to about 6% by dry weight of galactose units. The arabinoxylan can include about 3% to about 5% by dry weight of galactose units. The arabinoxylan can include less than about 1% by dry weight of mannose units. The arabinoxylan can include less than about 0.5% by dry weight of mannose units. The arabinoxylan can include arabinose units and xylose units, and a molar ratio of the arabinose units and xylose units can be about 0.05 to about 0.35. The arabinoxylan can include arabinose units and xylose units, and a molar ratio of the arabinose units and xylose units can be about 0.05 to about 0.15. The arabinoxylan can include arabinose units and xylose units, and a molar ratio of the arabinose units and xylose units can be about 0.15 to about 0.25. The arabinoxylan can include arabinose units and xylose units, and a molar ratio of the arabinose units and xylose units can be about 0.25 to about 0.35. The arabinoxylan can include arabinose units and xylose units, and a molar ratio of the arabinose units and xylose units can be about 0.06 to about 0.10. The arabinoxylan can include arabinose units and xylose units, and a molar ratio of the arabinose units and xylose units can be about 0.28 to about 0.32. The arabinoxylan can include glucose units and xylose units, and a molar ratio of the glucose units and xylose units can be about 0.10 to about 0.25. The arabinoxylan can include glucose units and xylose units, and a molar ratio of the glucose units and xylose units can be about 0.15 to about 0.25. The arabinoxylan can include glucose units and xylose units, and a molar ratio of the glucose units and xylose units can be about 0.10 to about 0.20. The arabinoxylan can include glucose units and xylose units, and a molar ratio of the glucose units and xylose units can be about 0.11 to about 0.15. The arabinoxylan can include glucose units and xylose units, and a molar ratio of the glucose units and xylose units can be about 0.18 to about 0.22. The composition can include less than about 1% by dry weight of carbohydrate polymers other than arabinoxylan. The composition can include less than about 0.5% by dry weight of carbohydrate polymers other than arabinoxylan. The composition can include about 0.5% to about 5% by dry weight of protein. The composition can include about 1% to about 4% by dry weight of protein. The composition can include about 0.8% to about 1.2% by dry weight of protein. The composition can include about 3.6% to about 4% by dry weight of protein. The composition can include about 0.5% to about 6% by dry weight of ash. The composition can include about 1% to about 5% by dry weight of ash. The composition can include about 1% to about 3% by dry weight of ash. The composition can include about 0.8% to about 1.2% by dry weight of ash. The composition can include about 4.5% to about 4.9% by dry weight of ash. The composition can have a molecular weight ($M_w$) of about 5500-6000 Da. The composition can have a molecular weight ($M_w$) of about 5500-5700 Da. The composition can have a molecular weight ($M_w$) of about 5600-5800 Da. The composition can have a molecular weight ($M_n$) of about 3000-3500 Da. The composition can have a molecular weight ($M_n$) of about 3200-3400 Da. The one or more polyphenols can include units selected from the group consisting of ferulic acid, gallic acid, 4-hydroxybenzoic acid, coumaric acid, syringic acid, sinapic acid, rosemarinic acid, vanillin, and combinations thereof. The composition can include about 0.001% to about 0.005% by dry weight of ferulic acid units. The composition can include about 0.001% to about 0.003% by dry weight of ferulic acid units. The composition can include about 0.01% to about 0.05% by dry weight of gallic acid units. The composition can include about 0.01% to about 0.03% by dry weight of gallic acid units. The composition can include about 1% to about 2% by dry weight of 4-hydroxybenzoic acid units. The composition can include about 1.0% to about 1.5% by dry weight of 4-hydroxybenzoic acid units. The composition can include about 0.01% to about 0.05% by dry weight of coumaric acid units. The composition can include about 0.01% to about 0.03% by dry weight of coumaric acid units. The composition can include about 0.05% to about 0.1% by dry weight of syringic acid units. The composition can include about 0.05% to about 0.07% by dry weight of syringic acid units. The composition can include about 0.1% to about 0.5% by dry weight of synapic acid units. The composition can include about 0.3% to about 0.5% by dry weight of synapic acid units. The composition can include about 0.05% to about 0.3% by dry weight of rosemarinic acid units. The composition can include about 0.1% to about 0.2% by dry weight of rosemarinic acid units. The composition can include about 0.001% to about 0.01% by dry weight of vanillin units. The composition can include about 0.004% to about 0.006% by dry weight of vanillin units. The composition can be light brown. The composition can have an antioxidant level of about 25000 to about 50000 μmol TE/100 g. The composition can have an antioxidant level of about 25000 to about 35000 μmol TE/100 g. The composition comprises epigallocatechin gallate.

In another aspect, provided herein is a composition including about 88% to about 90% by dry weight of arabinoxylan, wherein the arabinoxylan includes about 5% to about 7% by dry weight of arabinose units, about 78% to about 82% by dry weight of xylose units, about 9% to about 11% by dry weight of glucose units, about 3% to about 4% by dry weight of galactose units, about 4% to about 6% of carbohydrate polymers that are not arabinoxylan, sugar monomers, protein, ash, or a combination thereof, and about 3% to about 11% by dry weight of one or more polyphenols, wherein the molecular weight ($M_w$) of the composition can be about 5400 to about 5800 Da. In another aspect, provided herein is a composition including about 90% to about 94% by dry weight of arabinoxylan, wherein the arabinoxylan includes about 17% to about 21% by dry weight of arabinose units, about 62% to about 66% by dry weight of xylose units, about 12% to about 14% by dry weight of glucose units, about 3% to about 4% by dry weight of galactose units, about 8% to about 11% of carbohydrate polymers that are not arabinoxylan, sugar monomers, protein, ash, or a combination thereof, and about 1% to about 3% by dry weight of one or more polyphenols, wherein the molecular weight ($M_w$) of the composition can be about 5600 to about 6000 Da.

Implementations can include one or more of the following features. The molecular weight ($M_n$) of the composition can be about 3100 to about 3500 Da. The composition can include about 0.001% to about 0.003% by dry weight of ferulic acid units. The composition can include about 0.01% to about 0.02% by dry weight of gallic acid units. The composition can include about 1.0% to about 1.5% by dry weight of 4-hydroxybenzoic acid units. The composition can include about 0.01% to about 0.02% by dry weight of coumaric acid units. The composition can include about 0.05% to about 0.07% by dry weight of syringic acid units. The composition can include about 0.3% to about 0.5% by dry weight of sinapic acid units. The composition can include about 0.1% to about 0.2% by dry weight of rosemarinic acid units. The composition can include about 0.004% to about 0.006% by dry weight of vanillin units. The composition can have an antioxidant level of about 27000 to about 31000 μmol TE/100 g. The composition can include epigallocatechin gallate.

In another aspect provided herein is a food product including any one or more of the compositions provided herein.

In another aspect, provided herein is a dietary supplement including any one or more of the compositions provided herein.

In another aspect, provided herein is a pharmaceutical composition including any one or more of the compositions provided herein.

In another aspect, provided herein is a use of any one or more of the compositions provided herein in a food product.

In another aspect, provided herein is a use of any one or more of the compositions provided herein in a dietary supplement.

In another aspect, provided herein is a use of any one or more of the compositions provided herein in a pharmaceutical composition.

In another aspect, provided herein is a method of preparing a composition including providing a lignocellulosic biomass, combining the lignocellulosic biomass with water, activating the lignocellulosic biomass and water using conditions comprising at a first temperature and a first pressure to form a first activated cellulose stream, washing the first activated cellulose stream to form a washed first activated cellulose stream and a first soluble extract, wherein the first soluble extract comprises arabinoxylan, and processing the first soluble extract to form a composition.

Implementations can include one or more of the following features. The first temperature can be about 190° C. to about 215° C. The first pressure can be about 200 to about 500 psig. The activating step can have a duration of about 1 to about 30 minutes. Washing can include washing with water at a temperature of about 40° C. and about 100° C. Processing can include one or more of treating with carbon, nanofiltering, or a combination thereof. Treating with carbon can include treating with activated carbon. Threating with carbon can include using carbon in an amount of about 0.05% to about 0.15% by dry weight of the arabinoxylan in the first soluble extract. Processing can include sequentially, treating with carbon and nanofiltering to form the composition. The method can further include prior to processing, adding a reduced-mass arabinoxylan to the first soluble extract. The method can further include drying the composition. The composition can include 88% to about 99% by dry weight of arabinoxylan, about 5% to about 12% by dry weight of carbohydrate polymers other than arabinoxylan, sugar monomers, protein, ash, or a combination thereof, and about 1% to about 12% by dry weight of one or more polyphenols. The composition can include about 88% to about 90% by dry weight of arabinoxylan. The composition can include about 90% to about 99% by dry weight of arabinoxylan. The composition can include about 90% to about 95% by dry weight of arabinoxylan. The composition can include about 91% to about 93% by dry weight of arabinoxylan. The composition can include about 6% to about 10% by dry weight of carbohydrate polymers other than arabinoxylan, sugar monomers, protein, ash, or a combination thereof. The composition can include about 5% to about 7% by dry weight of carbohydrate polymers other than arabinoxylan, sugar monomers, protein, ash, or a combination thereof. The composition can include about 8% to about 10% by dry weight of carbohydrate polymers other than arabinoxylan, sugar monomers, protein, ash, or a combination thereof. The composition can include about 2% to about 5% by dry weight of one or more polyphenols. The composition can include about 5% to about 10% by dry weight of one or more polyphenols. The composition can include about 1% to about 3% by dry weight of one or more polyphenols. The composition can include about 1% to about 2% by dry weight of one or more polyphenols. The arabinoxylan can include about 5% to about 25% by dry weight of arabinose units. The arabinoxylan can include about 5% to about 15% by dry weight of arabinose units. The arabinoxylan can include about 10% to about 20% by dry weight of arabinose units. The arabinoxylan can include about 15% to about 25% by dry weight of arabinose units. The arabinoxylan can include about 5% to about 7% by dry weight of arabinose units. The arabinoxylan can include about 18% to about 20% by dry weight of arabinose units. The arabinoxylan can include about 60% to about 85% by dry weight of xylose units. The arabinoxylan can include about 60% to about 70% by dry weight of xylose units. The arabinoxylan can include about 70% to about 80% by dry weight of xylose units. The arabinoxylan can include about 75% to about 85% by dry weight of xylose units. The arabinoxylan can include about 62% to about 66% by dry weight of xylose units. The arabinoxylan can include about 78% to about 82% by dry weight of xylose units. The arabinoxylan can include about 8% to about 15% by dry weight of glucose units. The arabinoxylan can include about 10% to about 15% by dry weight of glucose units. The arabinoxylan can include about 9% to about 11% by dry weight of glucose units. The arabinoxylan can include about 12% to about 14% by dry weight of glucose units. The arabinoxylan can include about 2% to about 6% by dry weight of galactose units. The arabinoxylan can include about 3% to about 5% by dry weight of galactose units. The arabinoxylan can include less than about 1% by dry weight of mannose units. The arabinoxylan can include less than about 0.5% by dry weight of mannose units. The arabinoxylan can include arabinose units and xylose units, and a molar ratio of the arabinose units and xylose units can be about 0.05 to about 0.35. The arabinoxylan can include arabinose units and xylose units, and a molar ratio of the arabinose units and xylose units can be about 0.05 to about 0.15. The arabinoxylan can include arabinose units and xylose units, and a molar ratio of the arabinose units and xylose units can be about 0.15 to about 0.25. The arabinoxylan can include arabinose units and xylose units, and a molar ratio of the arabinose units and xylose units can be about 0.25 to about 0.35. The arabinoxylan can include arabinose units and xylose units, and a molar ratio of the arabinose units and xylose units can be about 0.06 to about 0.10. The arabinoxylan can include arabinose units and xylose units, and a molar ratio of the arabinose units and xylose units can be about 0.28 to about 0.32. The arabinoxylan can include glucose units and xylose units, and a molar ratio of the glucose units and xylose units can be about 0.10 to about 0.25. The arabinoxylan can include glucose units and xylose units, and a molar ratio of the glucose units and xylose units can be about 0.15 to about 0.25. The arabinoxylan can include glucose units and xylose units, and a molar ratio of the glucose units and xylose units can be about 0.10 to about 0.20. The arabinoxylan can include glucose units and xylose units, and a molar ratio of the glucose units and xylose units can be about 0.11 to about 0.15. The arabinoxylan can include glucose units and xylose units, and a molar ratio of the glucose units and xylose units can be about 0.18 to about 0.22. The composition can include less than about 1% by dry weight of carbohydrate polymers other than arabinoxylan. The composition can include less than about 0.5% by dry weight of carbohydrate polymers other than arabinoxylan. The composition can include about 0.5% to about 5% by dry weight of protein. The composition can include about 1% to about 4% by dry weight of protein. The composition can include about 0.8% to about 1.2% by dry weight of protein. The composition can include about 3.6% to about 4% by dry weight of protein. The composition can include about 0.5% to about 6% by dry weight of ash. The composition can include about 1% to about 5% by dry weight of ash. The composition can include about 1% to about 3% by dry weight of ash. The composition can include about 0.8% to about 1.2% by dry weight of ash. The composition can include about 4.5% to about 4.9% by dry weight of ash. The composition can have a molecular weight ($M_w$) of about 5500-6000 Da. The composition can have a molecular weight ($M_w$) of about 5500-5700 Da. The composition can have a molecular weight ($M_w$) of about 5600-5800 Da. The composition can have a molecular weight ($M_n$) of about 3000-3500 Da. The composition can have a molecular weight ($M_n$) of about 3200-3400 Da. The one or more polyphenols can include units selected from the group consisting of ferulic acid, gallic acid, 4-hydroxybenzoic acid, coumaric acid, syringic acid, sinapic acid, rosemarinic acid, vanillin, and combinations thereof. The composition can include about 0.001% to about 0.005% by dry weight of ferulic acid units. The composition can include about 0.001% to about 0.003% by dry weight of ferulic acid units. The composition can include about 0.01% to about 0.05% by dry weight of gallic acid units. The composition can include about 0.01% to about 0.03% by dry weight of gallic acid units. The composition can include about 1% to about 2% by dry weight of 4-hydroxybenzoic acid units. The composition can include about 1.0% to about 1.5% by dry weight of 4-hydroxybenzoic acid units. The composition can include about 0.01% to about 0.05% by dry weight of coumaric acid units. The composition can include about 0.01% to about 0.03% by dry weight of coumaric acid units. The composition can include about 0.05% to about 0.1% by dry weight of syringic acid units. The composition can include about 0.05% to about 0.07% by dry weight of syringic acid units. The composition can include about 0.1% to about 0.5% by dry weight of synapic acid units. The composition can include about 0.3% to about 0.5% by dry weight of synapic acid units. The composition can include about 0.05% to about 0.3% by dry weight of rosemarinic acid units. The composition can include about 0.1% to about 0.2% by dry weight of rosemarinic acid units. The composition can include about 0.001% to about 0.01% by dry weight of vanillin units. The composition can include about 0.004% to about 0.006% by dry weight of vanillin units. The composition can be light brown. The composition can have an antioxidant level of about 25000 to about 50000 µmol TE/100 g. The composition can have an antioxidant level of about 25000 to about 35000 µmol TE/100 g. The composition can include epigallocatechin gallate.

In another aspect, provided herein is a composition prepared by any of the methods provided herein.

In another aspect, provided herein is a food product including a composition prepared by any one of the methods provided herein.

In another aspect, provided herein is a pharmaceutical composition including a composition prepared by any of the methods provided herein.

In another aspect, provided herein is a dietary supplement including a composition prepared by any of the methods provided herein.

In another aspect, provided herein is a use of a composition prepared by any of the methods provided herein in a food product.

In another aspect, provided herein is a use of a composition prepared by any of the methods provided herein in a pharmaceutical composition.

In another aspect, provided herein is a use of a composition prepared by any of the methods provided herein in a dietary supplement.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF THE DRAWINGS

FIG. 1 is a diagram of an exemplary method for processing lignocellulosic biomass according to some embodiments.

DETAILED DESCRIPTION

This document provides compositions containing arabinoxylan, methods for making compositions containing arabinoxylan, and methods for using compositions containing arabinoxylan as, for example, a food ingredient, dietary supplement ingredient, or pharmaceutical ingredient. For example, this document provides compositions (e.g., arabinoxylan compositions) containing predominately arabinoxylan (e.g., greater than 88% percent arabinoxylan by dry weight) that has a molecular weight ($M_w$) of about 5500 Da to about 6000 Da.

Arabinoxylan is a heteropolymer found in many plants that can include any appropriate units. Typically, arabinoxylan has a xylose backbone (e.g., 1,4-linked xylose) which is covalently linked to one or more arabinose units (e.g., via a 2,3-linkage). Arabinoxylan can be further covalently linked to other sugar units, such as glucose, galactose, and maltose, or to polyphenols or polyphenol units. In some cases, arabinoxylan can be described based on its constituent units (e.g., by dry weight). By way of example only, a particular arabinoxylan can be described as about 18% arabinose, about 63% xylose, about 13% glucose, about 4% galactose, and about 2% polyphenols, all by dry weight.

In some cases, a composition (e.g., an arabinoxylan composition) provided herein can have an arabinoxylan content of about 88% to about 95% by dry weight, where the molecular weight ($M_w$) of the arabinoxylan of the composition is about 5500 to about 6000 Da, and where the composition has (a) a content of carbohydrate polymers that are not arabinoxylan less than about 1% by dry weight and (b) a polyphenol content of about 1% to about 3% by dry weight.

In some cases, a composition (e.g., an arabinoxylan composition) provided herein can have an arabinoxylan content of about 80% to about 95% by dry weight, where the molecular weight ($M_w$) of the arabinoxylan of the composition is about 3100 to about 8400 Da, and where the composition has (a) a content of carbohydrate polymers that are not arabinoxylan less than about 1% by dry weight and (b) a polyphenol content of about 1% to about 14% by dry weight. In some cases, a composition (e.g., an arabinoxylan composition) provided herein can have an arabinoxylan content of about 80% to about 95% by dry weight, where the molecular weight ($M_w$) of the arabinoxylan of the composition is about 3100 to about 8400 Da, and where the composition has (a) a content of other carbohydrate polymers that are not arabinoxylan, monomers, protein, and ash, of about 5% to about 20% by dry weight and (b) a polyphenol content of about 1% to about 14% by dry weight.

As described herein, plant material can be processed as described herein to produce compositions (e.g., arabinoxylan compositions) that (a) contain predominately arabinoxylan (e.g., greater than 88 percent arabinoxylan by dry weight) that has a molecular weight ($M_w$) of about 5500 to about 6000 Da and (b) have other desirable structural and/or functional characteristics such as a content of carbohydrate polymers that are not arabinoxylan less than about 1%, a polyphenol content of about 1% to about 12% by dry weight, a content of ferulic acid units (e.g., as components of polyphenols, free units, or a combination thereof) of 0.0005% to about 0.005%, a content of gallic acid units (e.g., as components of polyphenols, free units, or a combination thereof) of about 0.005% to about 0.02%, a content of epigallocatechin-3-gallate units, and/or a color (e.g., when in powder form) of light brown.

As described herein, plant material can be processed as described herein to produce compositions (e.g., arabinoxylan compositions) that (a) contain predominately arabinoxylan (e.g., greater than 80 percent arabinoxylan by dry weight) that has a molecular weight ($M_w$) of about 3100 to about 8400 Da and (b) have other desirable structural and/or functional characteristics such as a content of carbohydrate polymers that are not arabinoxylan less than about 1%, a polyphenol content of about 1% to about 14% by dry weight, a content of ferulic acid units (e.g., as components of polyphenols, free units, or a combination thereof) of 0.0005% to about 0.005%, a content of gallic acid units (e.g., as components of polyphenols, free units, or a combination thereof) of about 0.005% to about 0.02%, a content of epigallocatechin-3-gallate units, and/or a color (e.g., when in powder form) of light brown. As described herein, plant material can be processed as described herein to produce compositions (e.g., arabinoxylan compositions) that (a) contain predominately arabinoxylan (e.g., greater than 80 percent arabinoxylan by dry weight) that has a molecular weight ($M_w$) of about 3100 to about 8400 Da and (b) have other desirable structural and/or functional characteristics such as a content of other carbohydrate polymers that are not arabinoxylan, monomers, protein, and ash, of about 5% to about 20% by dry weight, a polyphenol content of about 1% to about 14% by dry weight, a content of ferulic acid units (e.g., as components of polyphenols, free units, or a combination thereof) of 0.0005% to about 0.005%, a content of gallic acid units (e.g., as components of polyphenols, free units, or a combination thereof) of about 0.005% to about 0.02%, a content of epigallocatechin-3-gallate units, and/or a color (e.g., when in powder form) of light brown.

This document provides compositions including arabinoxylan (e.g., arabinoxylan compositions). A composition described herein can include arabinoxylan and any other appropriate components. In some cases, a composition described herein can include polyphenols. In some cases, a composition described herein can include carbohydrate polymers that are not arabinoxylan, sugar monomers, ash, protein, or a combination thereof.

A composition described herein can include arabinoxylan in any appropriate amount. Various references to percentage of components of the composition appear throughout this document. The percentages are percent by dry weight unless otherwise indicated. In some embodiments, a composition described herein can include about 80% to about 99% by dry weight of arabinoxylan (e.g., about 80% to about 97%, about 80% to about 95%, about 80% to about 93%, about 80% to about 90%, about 90% to about 99%, about 93% to about 99%, about 95% to about 99%, about 90% to about 95%, or about 91% to about 93% by dry weight of arabinoxylan). In some embodiments, a composition described herein can include about 88% to about 99% by dry weight of arabinoxylan (e.g., about 88% to about 97%, about 88% to about 95%, about 88% to about 93%, about 88% to about 90%, about 90% to about 99%, about 93% to about 99%, about 95% to about 99%, about 90% to about 94%, about 90% to about 95%, or about 91% to about 93% by dry weight of arabinoxylan). In some embodiments, a composition described herein can include at least about 80% by dry weight of arabinoxylan (e.g., at least about 83%, at least about 85%, at least about 89%, at least about 91%, at least about 93%, at least about 95%, or at least about 97% by dry weight of arabinoxylan).

The arabinoxylan of a composition described herein (e.g., an arabinoxylan composition) can have any appropriate molecular weight. A molecular weight can be determined by any appropriate method. For example, a molecular weight can be determined using size exclusion (sometimes also called gel permeation) chromatography (SEC). Size exclusion chromatography can be used to separate complex mixtures of macromolecules according to their hydrodynamic size. In some embodiments, the arabinoxylan of a composition described herein (e.g., an arabinoxylan composition) can have a molecular weight (as $M_w$) of about 3100 to about 8400 Da (e.g., 3100 to about 3500 Da, about 3100 to about 4000 Da, about 3100 to about 4800 Da, about 3100 to about 5500 Da, about 5500 to about 7500 Da, about 4500 to about 6500 Da, or about 6500 to about 8400 Da). In some embodiments, the arabinoxylan of a composition described herein (e.g., an arabinoxylan composition) can have a molecular weight (as $M_w$) of at least about 4800 Da (e.g., at least about 4900 Da, at least about 5000 Da, at least about 5200 Da, at least about 5400 Da, at least about 5600 Da, or at least about 5800 Da). For example, the arabinoxylan of a composition described herein (e.g., an arabinoxylan composition) can have a molecular weight (as $M_w$) of about 5400 to about 6000 Da (e.g., about 5500 to about 6000 Da, about 5400 to about 5800 Da, about 5500 to about 5900 Da, about 5500 to about 5700 Da, about 5600 to about 5800 Da, about 5600 to about 6000 Da, about 5700 to about 6000 Da, or about 5700 to about 5900 Da). In some embodiments, the arabinoxylan of a composition described herein (e.g., an arabinoxylan composition) can have a molecular weight (as $M_n$) of about 3000 to about 3500 Da (e.g., about 3000 to about 3400 Da, about 3000 to about 3300 Da, about 3200 Da to about 3400 Da, about 3200 Da to about 3500 Da, about 3300 Da to about 3500 Da, about 3100 Da to about 3500 Da, or about 3200 Da to about 3300 Da).

Arabinoxylan in a composition described herein (e.g., an arabinoxylan composition) can have any appropriate chemical makeup (e.g., including arabinose units, xylose units, glucose units, galactose units, mannose units, polyphenol units, or a combination thereof). The chemical makeup can be determined by any appropriate method such as the method described in Technical Report NREL/TP-510-42623 (January 2008) published by the National Renewable Energy Laboratory (U.S. Dept. of Energy) titled, "Determination of Sugars, Byproducts, and Degradation Products in Liquid Fraction Process Samples", incorporated herein by reference in its entirety. For example, the arabinoxylan of a composition provided herein can include about 5% to about 40% (e.g., about 5% to about 35%, about 5% to about 30%, about 5% to about 25%, about 5% to about 7%, about 5% to about 10%, about 5% to about 20%, about 5% to about 15%, about 5% to about 10%, about 5% to about 7%, about 10% to about 20%, about 10% to about 25%, about 15% to about 25%, about 17% to about 21%, about 20% to about 25%, about 10% to about 40%, about 15% to about 40%, about 20% to about 40%, about 25% to about 40%, about 30% to about 40%, about 35% to about 40%, about 10% to about 20%, about 15% to about 20%, or about 18% to about 20%) by dry weight of arabinose units. In some cases, the arabinoxylan of a composition provided herein can include about 60% to about 85% (e.g., about 60% to about 80%, about 60% to about 70%, about 70% to about 80%, about 60% to about 65%, about 62% to about 66%, about 70% to about 85%, about 75% to about 85%, about 80% to about 85%, about 63% to about 65%, about 62% to about 66%, about 72% to about 82%, about 78% to about 82%, about 79% to about 81%) by dry weight of xylose units. In some cases, the arabinoxylan of a composition provided herein can include about 5% to about 20% (e.g., about 5% to about 15%, about 5% to about 10%, about 10% to about 20%, about 10% to about 15%, about 8% to about 12%, about 8% to about 15%, about 9% to about 11%, about 11% to about 15%, or about 12% to about 14%) by dry weight of glucose units. In some cases, the arabinoxylan of a composition provided herein can include about 2% to about 6% (e.g., about 3% to about 4% or about 3% to about 5%) by dry weight of galactose units. In some cases, the arabinoxylan of a composition provided herein can include less than about 1% (e.g., less than about 0.8%, 0.6%, 0.5%, 0.4%, 0.3%, 0.1%, 0.05%, or 0.01%) by dry weight of mannose units. In some embodiments, the arabinoxylan of a composition provided herein can lack mannose or contain very little mannose. For example, the arabinoxylan of a composition provided herein can include about 0% to about 1% (e.g., about 0% to about 0.5%, about 0% to about 0.1%, about 0% to about 0.05%, about 0% to about 0.01%, or about 0.5% to about 1%) by dry weight of mannose units. In some embodiments, the arabinoxylan of a composition provided herein can lack mannose. These components can be present in the arabinoxylan of a composition provided herein in any appropriate ratio. In some embodiments, the ratio of arabinose units to xylose units of the arabinoxylan of a composition provided herein can be about 0.05 to about 0.65 (e.g., about 0.05 to about 0.25, about 0.25 to about 0.45, or about 0.45 to about 0.65). For example, the ratio of arabinose units to xylose units of the arabinoxylan of a composition provided herein can be about 0.05 to about 0.35 (e.g., about 0.05 to about 0.25, about 0.05 to about 0.15, about 0.05 to about 0.10, about 0.10 to about 0.35, about 0.15 to about 0.25, about 0.15 to about 0.35, about 0.25 to about 0.35, about 0.06 to about 0.10, about 0.07 to about 0.09, about 0.28 to about 0.32, or about 0.29 to about 0.31). In some embodiments, the ratio of glucose units to xylose units of the arabinoxylan of a composition provided herein can be about 0.10 to about 0.25 (e.g., about 0.10 to about 0.20, about 0.10 to about 0.15, about 0.11 to about 0.15, about 0.15 to about 0.25, about 0.15 to about 0.20, about 0.18 to about 0.22 or about 0.20 to about 0.25).

Polyphenols (e.g., one or more polyphenols) can be present in a composition provided herein (e.g., an arabinoxylan composition) in any appropriate amount. In some embodiments, a composition described herein (e.g., an arabinoxylan composition) can include about 1% to about 14% (e.g., about 1% to about 12%, about 1% to about 10%, about 1% to about 5%, about 1% to about 3%, about 1% to about 2%, about 2% to about 5%, about 2% to about 12%, about 5% to about 10%, about 5% to about 12%, about 8% to about 12%, about 2% to about 14%, about 5% to about 14%, about 8% to about 14%, about 10% to about 14%, about 2% to about 8%, about 3% to about 11%, or about 4% to about 6%) by dry weight of one or more polyphenols.

A composition described herein (e.g., an arabinoxylan composition) can include polyphenol units. In some cases, polyphenol units can be part of polyphenols. In some embodiments, polyphenols of a composition provided herein can be covalently attached to the arabinoxylan of the composition, can be free polyphenols, or can be a combination thereof. In some cases, polyphenol units can be free units. In some embodiments, polyphenols can be predominantly attached to the arabinoxylan. In some embodiments, polyphenol units can include ferulic acid, gallic acid, 4-hydroxybenzoic acid, coumaric acid, syringic acid, sinapic acid, rosemarinic acid, vanillin, or combinations thereof. Polyphenol units of a composition provided herein can be present in any appropriate amount. The polyphenol units of a composition provided herein can be measured using any appropriate method such as the methods described in Malunga, Lovemore Nkhata, and Trust Beta. "Antioxidant capacity of water☐extractable arabinoxylan from commercial barley, wheat, and wheat fractions." *Cereal Chemistry* 92.1 (2015): 29-36 or Nour, Violeta, Ion Trandafir, and Sina Cosmulescu. "HPLC determination of phenolic acids, flavonoids and juglone in walnut leaves." *Journal of Chromatographic Science* 51.9 (2013): 883-890, both of which are herein incorporated by reference in their entireties. In some cases, standards can be purchased from a supplier such as Sigma-Aldrich, and an Agilent 1260 with quaternary pump, autosampler, and multiwavelength detector (HPLC-UV) can be used for detection. In some embodiments, a composition described herein (e.g., an arabinoxylan composition) can include ferulic acid units. Ferulic acid units can be present in any appropriate amount. In some embodiments, a composition described herein (e.g., an arabinoxylan composition) can include about 0.0005% to about 0.005%

(e.g., about 0.0005% to about 0.001%, about 0.001% to about 0.003%, about 0.001% to about 0.005%, about 0.003% to about 0.005%, or about 0.001% to about 0.003%) by dry weight of ferulic acid units. In some embodiments, a composition described herein (e.g., an arabinoxylan composition) can include gallic acid units. Gallic acid units can be present in any appropriate amount. In some embodiments, a composition described herein (e.g., an arabinoxylan composition) can include about 0.005% to about 0.05% (e.g., about 0.005% to about 0.01%, about 0.01% to about 0.02%, about 0.01% to about 0.03%, or about 0.01% to about 0.05%) by dry weight of gallic acid units. In some embodiments, a composition described herein (e.g., an arabinoxylan composition) can include 4-hydroxybenzoic acid units. 4-hydroxybenzoic acid units can be present in any appropriate amount. In some embodiments, a composition described herein (e.g., an arabinoxylan composition) can include about 0.5% to about 2% (e.g., about 0.5% to about 1%, about 1% to about 2%, about 1.0% to about 1.5%, about 1.1% to about 1.5%, or about 1.2% to about 1.4%) by dry weight of 4-hydroxybenzoic acid units. In some embodiments, a composition described herein (e.g., an arabinoxylan composition) can include coumaric acid units. Coumaric acid units can be present in any appropriate amount. In some embodiments, a composition described herein (e.g., an arabinoxylan composition) can include about 0.010% to about 0.05% (e.g., about 0.01% to about 0.02%, about 0.01% to about 0.03%, about 0.010% to about 0.015%, about 0.010% to about 0.025%, about 0.020% to about 0.025%, about 0.015% to about 0.025%, about 0.014% to about 0.018%, about 0.015% to about 0.017%) by dry weight of coumaric acid units. In some embodiments, a composition described herein (e.g., an arabinoxylan composition) can include syringic acid units. Syringic acid units can be present in any appropriate amount. In some embodiments, a composition described herein (e.g., an arabinoxylan composition) can include about 0.01% to about 0.1% (e.g., about 0.01% to about 0.08%, about 0.01% to about 0.05%, about 0.01% to about 0.03%, about 0.03% to about 0.1%, about 0.05% to about 0.1%, about 0.08% to about 0.1%, about 0.04% to about 0.08%, or about 0.05% to about 0.07%) by dry weight of syringic acid units. In some embodiments, a composition described herein (e.g., an arabinoxylan composition) can include synapic acid units. Synapic acid units can be present in any appropriate amount. In some embodiments, a composition described herein (e.g., an arabinoxylan composition) can include about 0.1% to about 0.6% (e.g., about 0.2% to about 0.6%, about 0.2% to about 0.5%, about 0.2% to about 0.3%, about 0.3% to about 0.6%, about 0.5% to about 0.6%, about 0.1% to about 0.5%, or about 0.3% to about 0.5%) by dry weight of synapic acid units. In some embodiments, a composition described herein (e.g., an arabinoxylan composition) can include rosemarinic acid units. Rosemarinic acid units can be present in any appropriate amount. In some embodiments, a composition described herein (e.g., an arabinoxylan composition) can include about 0.05% to about 0.3% (e.g., about 0.05% to about 0.02%, about 0.05% to about 0.1%, about 0.1% to about 0.3%, about 0.1% to about 0.5%, or about 0.1% to about 0.2%) by dry weight of rosemarinic acid units. In some embodiments, a composition described herein (e.g., an arabinoxylan composition) can include vanillin units. Vanillin units can be present in any appropriate amount. In some embodiments, vanillin units can be present in an amount of about 0.001% to about 0.01% (e.g., about 0.001% to about 0.008%, about 0.001% to about 0.005%, about 0.001% to about 0.003%, about 0.003% to about 0.01%, about 0.005% to about 0.1%, about 0.001% to about 0.007%, or about 0.004% to about 0.006%) by dry weight of vanillin units. In some embodiments, a composition described herein (e.g., an arabinoxylan composition) can include epigallochatechin gallate (EGCG) units. In some embodiments, a composition described herein (e.g., an arabinoxylan composition) can include EGCG units. EGCG units can be present in any appropriate amount.

A composition described herein (e.g., an arabinoxylan composition) can have any appropriate antioxidant level. An antioxidant level can be measured using any appropriate method. For example, the micromole trolox equivalent per 100 grams µmol TE/100 g) of a composition described herein (e.g., an arabinoxylan composition) can be determined. In some embodiments, a composition can have an antioxidant level of about 25000 to about 50000 (e.g., about 25000 to about 35000, about 25000 to about 30000, about 30000 to about 35000, about 30000 to about 50000, about 40000 to about 50000, about 27000 to about 31000, or about 28000 to about 30000) µmol TE/100 g.

As described herein, a composition provided herein (e.g., an arabinoxylan composition) can have arabinoxylan as a primary component. In some cases, a composition described herein (e.g., an arabinoxylan composition) can be characterized by the amounts of components other than arabinoxylan, such as carbohydrate polymers other than arabinoxylan, sugar monomers, protein, ash or a combination thereof. Non-limiting examples of carbohydrate polymers other than arabinoxylan include cellulose, amylose, amylopectin, glucuronoxylan, glucuronoarabinoxylan, and glucomannan. For example, in some embodiments, a composition described herein (e.g., an arabinoxylan composition) can include less than 10% (e.g., less than 9%, 8%, 7%, 6%, 5%, 4%, 3%, 2%, or 1%) by dry weight of a combination of carbohydrate polymers other than arabinoxylan, sugar monomers, protein, and ash. In some embodiments, a composition described herein (e.g., an arabinoxylan composition) can include about 4% to about 20% (e.g., about 4% to about 12%, about 4% to about 10%, about 4% to about 6%, about 5% to about 7%, about 5% to about 10%, about 6% to about 10%, about 5% to about 15%, about 8% to about 10%, about 8% to about 11%, about 10% to about 20%, or about 15% to about 20%) by dry weight of a combination of carbohydrate polymers other than arabinoxylan, sugar monomers, protein, and ash. In some embodiments, a composition described herein (e.g., an arabinoxylan composition) can include about 4% to about 12% (e.g., about 4% to about 10%, about 4% to about 8%, about 4% to about 6%, about 5% to about 12%, about 8% to about 12%, about 9% to about 12%, about 5% to about 10%, about 4% to about 6%, or about 9% to about 10%) by dry weight of a combination of carbohydrate polymers other than arabinoxylan, sugar monomers, protein, and ash. In some embodiments, a composition described herein (e.g., an arabinoxylan composition) can include less than about 1% (e.g., less than about 0.8%, 0.6%, 0.5%, 0.4%, 0.2%, 0.1%, 0.05%, or 0.01%) by dry weight of carbohydrate polymers other than arabinoxylan. In some embodiments, a composition described herein (e.g., an arabinoxylan composition) can include about 0% to about 1% (e.g., about 0% to about 0.5%, about 0% to about 0.1%, about 0% to about 0.05%, about 0% to about 0.01%, or about 0.5% to about 1%) by dry weight of carbohydrate polymers other than arabinoxylan. In some embodiments, a composition described herein (e.g., an arabinoxylan composition) can include about 0% to about 5% (e.g., about 0% to about 3%, about 0% to about 2%, about 1% to about 5%, about 3% to about 5%, or about 3% to about 5%) by dry weight of sugar monomers. In some embodiments, a composition described herein (e.g., an arabinoxylan composition) can include about 0.5% to about 5% (e.g., about 0.5% to about 3%, about 0.5% to about 1%, about 0.8% to about 1.2%, about 1% to about 5%, about 3% to about 5%, about 1% to about 4%, about 2% to about 4%, about 3% to about 4%, or about 3.6% to about 4%) by dry weight of protein. In some embodiments, a composition described herein (e.g., an arabinoxylan composition) can include about 0.5% to about 6% (e.g., about 0.5% to about 5%, about 0.8% to about 1.2%, about 1% to about 3%, about 1% to about 5%, about 1% to about 6%, about 3% to about 6%, about 4% to about 5%, about 4.5% to about 4.9%, or about 5% to about 6%) by dry weight of ash.

In some cases, a composition described herein (e.g., an arabinoxylan composition) can be designed to have little, if any, amounts of one or more particular components. For example, a composition described herein (e.g., an arabinoxylan composition) can be designed to lack one or more particular components (e.g., one or more particular components that may be present within starting material used to produce the composition). Such compositions can have improved odor or smell properties, improved or desirable visual appearance or color, and/or improved tastes or flavors as compared to the starting material. In some cases, a composition described herein (e.g., an arabinoxylan composition) can have a decreased amount of one or more components that may be present in a starting material (e.g., a lignocellulosic biomass). Corn syrups are common sweeteners, and compositions described herein can, in some embodiments, have different components than corn syrups. For example, in some cases, corn syrups can include maltose, maltotriose, or a combination thereof.

Accordingly, in some embodiments, a composition described herein (e.g., an arabinoxylan composition) can lack maltose, maltotriose, or a combination thereof. In some embodiments, a composition described herein (e.g., an arabinoxylan composition) can include maltose in an amount of less than about 15% by dry weight of (e.g., less than about 12%, 10%, 5%, 2%, or 1% by dry weight). In some embodiments, a composition as described herein (e.g., an arabinoxylan composition) can include maltotriose in an amount of less than about 15% by dry weight of (e.g., less than about 12%, 10%, 5%, 2%, or 1% by dry weight).

A composition described herein (e.g., an arabinoxylan composition) can have any appropriate color. Without being bound by any particular theory, it is believed that polyphenols can contribute to the color of a composition to make it browner; consequently, a lighter-colored composition is believed to be lower in polyphenol content than a darker-colored composition. In some embodiments, a composition can be brown. In some embodiments, a composition (e.g., an arabinoxylan composition) can be light brown.

This document also provides particular exemplary arabinoxylan compositions. For example, this document provides an exemplary composition including: about 88% to about 90% (e.g., about 89%) by dry weight of arabinoxylan; less than about 1% (e.g., less than about 0.5% or 0.1%) by dry weight of carbohydrate polymers other than arabinoxylan; about 3% to about 5% (e.g., about 4%) by dry weight of sugar monomers; about 0.5% to about 1.5% (e.g., about 1%) by dry weight of protein; about 0.5% to about 1.5% (e.g., about 1%) by dry weight of ash; and about 2% to about 12% by dry weight of polyphenols. The arabinoxylan in this exemplary composition can have a molecular weight ($M_w$) of about 5500 to about 5700 Da (e.g., about 5600 Da). The arabinoxylan in this composition can have a content of: about 5% to about 7% (e.g., about 6%) by dry weight of arabinose units, about 78% to about 82% (e.g., about 79% to about 81% or about 82%) by dry weight of xylose units, about 9% to about 11% (e.g., about 10%) by dry weight of glucose units, about 3% to about 5% (e.g., about 4%) by dry weight of galactose units, and less than about 1% (e.g., less than about 0.5% or 0.1%) by dry weight of mannose units. The composition can be light brown.

As another example, this document provides another exemplary composition including: about 91% to about 93% by dry weight of arabinoxylan, less than about 1% (e.g., less than about 0.5% or 0.1%) by dry weight of carbohydrate polymers other than arabinoxylan; about 0.5% to about 1.5% (e.g., about 1%) of sugar monomers; about 3% to about 4% (e.g., about 3.8%) by dry weight of protein; about 4% to about 5% (e.g., about 4.7%) by dry weight of ash; and about 1% to about 3% (e.g., about 2%) by dry weight of polyphenols. The arabinoxylan in this exemplary composition can have a molecular weight ($M_w$) of about 5700 to about 5900 Da (e.g., about 5800 Da). The arabinoxylan in this exemplary composition can have a molecular weight ($M_n$) of about 3200 to about 3400 Da (e.g., about 3300 Da). The arabinoxylan in this composition can have a content of: about 18% to about 20% (e.g., about 19%) by dry weight of arabinose units; about 62% to about 66% (e.g., about 63% to about 65%, or about 64%) by dry weight of xylose units; about 12% to about 14% (e.g., about 13%) by dry weight of glucose units; about 3% to about 5% (e.g., about 4%) by dry weight of galactose units; and less than about 1% (e.g., less than about 0.5% or 0.1%) by dry weight of mannose units. The polyphenols in this composition can have a content of: about 0.001% to about 0.003% (e.g., about 0.002%) by dry weight of ferulic acid units; about 0.01% to about 0.02% (e.g., about 0.014%) by dry weight of gallic acid units; about 1% to about 2% (e.g., about 1.3%) by dry weight of 4-hydroxybenzoic acid units; about 0.01% to about 0.02% (e.g., about 0.016%) by dry weight of coumaric acid units; about 0.05% to about 0.07% (e.g., about 0.06%) by dry weight of syringic acid units; about 0.03% to about 0.05% (e.g., about 0.4%) by dry weight of sinapic acid units; about 0.05% to about 0.15% (e.g., 0.11%) by dry weight of rosemarinic acid units, and about 0.004% to about 0.006% (e.g., about 0.005%) by dry weight of vanillin units. The composition can be light brown.

In some cases, a composition provided herein (e.g., a composition having about 90% to about 94% by dry weight of arabinoxylan, wherein the arabinoxylan comprises about 17% to about 21% by dry weight of arabinose units; about 62% to about 66% by dry weight of xylose units; about 12% to about 14% by dry weight of glucose units; about 3% to about 4% by dry weight of galactose units; about 8% to about 11% of carbohydrate polymers that are not arabinoxylan, sugar monomers, protein, ash, or a combination thereof; and about 1% to about 3% by dry weight of one or more polyphenols, wherein the molecular weight ($M_w$) of the composition is about 5600 to about 6000 Da, or Exemplary Composition 2 (Example 2)) can provide pre-biotic benefits. For example, it was surprisingly found that administration of a composition provided herein (e.g., a composition having about 90% to about 94% by dry weight of arabinoxylan, wherein the arabinoxylan comprises about 17% to about 21% by dry weight of arabinose units; about 62% to about 66% by dry weight of xylose units; about 12% to about 14% by dry weight of glucose units; about 3% to about 4% by dry weight of galactose units; about 8% to about 11% of carbohydrate polymers that are not arabinoxylan, sugar monomers, protein, ash, or a combination thereof; and about 1% to about 3% by dry weight of one or more polyphenols, wherein the molecular weight ($M_w$) of the composition is about 5600 to about 6000 Da, or Exemplary Composition 2 (Example 2)) at, for example, about 7 grams and about 14 grams in a single serving twice per day had a gastrointestinal tolerance that did not significantly differ from the gastrointestinal tolerance exhibited when a placebo composition was administered (see, e.g., Example 8). In contrast, fiber supplements (for example, arabinoxylan oligosaccharides (AXOS)) are generally thought to be less tolerated in the gastrointestinal system, causing, for example, gas and/or bloating, even when dosed at the lower level used in Example 8 (about 7 grams per serving). See, for example, Cloetens, Lieselotte, et al. "Tolerance of arabinoxylan-oligosaccharides and their prebiotic activity in healthy subjects: a randomised, placebo-controlled cross-over study." British Journal of Nutrition 103.5 (2010): 703-713 and François, Isabelle EJA, et al. "Effects of a wheat bran extract containing arabinoxylan oligosaccharides on gastrointestinal health parameters in healthy adult human volunteers: a double-blind, randomised, placebo-controlled, cross-over trial." British Journal of Nutrition 108.12 (2012): 2229-2242, incorporated herein by reference in their entireties.

This document also provides products comprising any one or more of the compositions described herein. For example, this document provides sweetener compositions comprising any one or more of the compositions described herein. In some cases, a food product can be designed to include one or more of the compositions described herein. In some cases, a pharmaceutical composition or dietary supplement can be formulated to include one or more of the compositions described herein. Products comprising any one or more of the compositions provided herein can have advantages. Non-limiting examples of such advantages include a reduction in calories, reduction in glycemic index, provision of soluble fiber, provision of prebiotics, and provision of antioxidants. Without being bound by any particular theory, it is believed that arabinoxylan is a low-calorie carbohydrate, and that arabinoxylan is a source of soluble fiber that can be used by components of the microbiome to promote health. It is further believed that, in some cases, polyphenols and/or polyphenol units can act as antioxidants.

In any of the consumable compositions (e.g., sweetener compositions, food products, pharmaceutical compositions, or dietary supplements) provided herein, a composition as described herein can be present in any appropriate amount. For example, in some cases, a composition as described herein can be present in an amount of about 500 mg to about 15 g (e.g., about 500 mg to about 1 g, about 500 mg to about 3 g, about 500 mg to about 5 g, about 500 mg to about 7 g, about 500 mg to about 10 g, about 500 mg to about 12 g, about 1 g to about 15 g, about 3 g to about 15 g, about 5 g to about 15 g, about 7 g to about 15 g, about 10 g to about 15 g, about 12 g to about 15 g, about 5 g to about 10 g, or about 7 g to about 12 g) per serving. In some cases, a composition as described herein can be present in an amount of at least 7 g (e.g., at least 8 g, 10 g, 12 g, 14 g, or 15 g) per serving.

Calorie content, glycemic index, soluble fiber content, prebiotic fiber content, and antioxidant content can each be determined by any appropriate method. In some embodiments, the soluble fiber content can be the same as the arabinoxylan content (e.g., in percent by dry weight). In some embodiments, the prebiotic content can be the same as the arabinoxylan content e.g., in percent by dry weight). In some embodiments, the antioxidant content can be the same as the polyphenol content e.g., in percent by dry weight).

This document also provides uses of any one or more of the compositions described herein. For example, this document provides the use of any one or more of the compositions described herein in a sweetener composition, food product, pharmaceutical composition, and/or dietary supplement.

A sweetener composition can be any appropriate sweetener composition that is formulated to include one or more of the compositions containing arabinoxylan described herein. For example, a composition provided herein can be combined with a traditional sweetener (e.g., a corn syrup) to produce a reduced-calorie and/or reduced glycemic-index sweetener composition. Combining can include any appropriate steps. In some embodiments, combining can include mixing, blending, agitating, dissolving, emulsifying, or a combination thereof. For example, in some embodiments, dry glucose and a dry composition provided herein can be mixed together, and, optionally, water can be added to form a syrup (e.g., at about 70% to about 80% dry matter). In some embodiments, a dry composition provided herein can be added to a glucose syrup (e.g., by mixing, blending, dissolving, or a combination thereof). In some embodiments, dry glucose can be added to a composition provided herein in the form of a syrup (e.g., by mixing, blending, dissolving, or a combination thereof). In some embodiments, a glucose syrup can be combined (e.g., by mixing or blending) with a composition provided herein in the form of a syrup. One or more compositions (e.g., arabinoxylan compositions) as described herein can be combined with a traditional sweetener to form a sweetener. One or more compositions (e.g., arabinoxylan compositions) as described herein can be combined with a traditional sweetener in any appropriate ratio. For example, in some embodiments, a ratio of about 5% to about 90% (e.g., about 10% to about 90%, about 25% to about 90%, about 50% to about 90%, about 75% to about 90%, about 10% to about 25%, about 10% to about 50%, about 10% to about 75%, about 20% to about 80%, about 40% to about 60%, about 45% to about 55%, about 10% to about 30%, about 30% to about 50%, about 50% to about 70%, or about 70% to about 90%) by dry weight of or by volume of a composition provided herein (e.g., an arabinoxylan composition) can be combined with about 5% to about 90% (e.g., about 10% to about 90%, about 25% to about 90%, about 50% to about 90%, about 75% to about 90%, about 10% to about 25%, about 10% to about 50%, about 10% to about 75%, about 20% to about 80%, about 40% to about 60%, about 45% to about 55%, about 10% to about 30%, about 30% to about 50%, about 50% to about 70%, or about 70% to about 90%) by dry weight of or by volume of a traditional sweetener.

In some cases, a sweetener composition provided herein can have desirable properties. For example, in some embodiments, a sweetener composition can be a solid. In some embodiments, a sweetener composition can be a liquid. In some cases, a sweetener composition provided herein can have a dextrose equivalent (DE) of about 35 to about 75 (e.g., about 35 to about 65, about 35 to about 55, about 35 to about 45, about 45 to about 75, about 55 to about 75, about 65 to about 75, about 42, about 53, or about 63). Without being bound by any particular theory, it is believed that a sweetener composition described herein with a DE that is within about 10 percent as a commercially available sweetener may be substituted in approximately equal volume (or within about 10 percent) for the commercially available sweetener. In some embodiments, a sweetener composition provided herein can have a glycemic index (GI) of about 10 to about 80 (e.g., about 10 to about 75, about 10 to about 50, about 10 to about 25, about 25 to about 80, about 50 to about 80, about 75 to about 80, about 35 to about 50, about 40 to about 50, or about 40 to about 45). The glycemic index of glucose (e.g., dextrose) is typically reported to be 100. The glycemic index of sucrose is typically reported to be 65. Without being bound by any particular theory, it is believed that sweeteners with lower GI values can aid in management of blood sugar and insulin levels and/or be useful in controlling appetite and weight loss. In some embodiments, a sweetener composition provided herein can have a calorie content of about 100 to about 225 (e.g., about 100 to about 200, about 100 to about 175, about 100 to about 150, about 100 to about 125, about 125 to about 225, about 150 to about 225, about 175 to about 225, about 200 to about 225, about 125 to about 200, about 150 to about 200, about 175 to about 200, or about 180 to about 200) per 100 g of the sweetener composition.

Properties described can be measured using any appropriate method. For example, a glycemic index (GI) can be measured using methods known in the art, for example, as described in "In vitro method for predicting glycemic index of foods using simulated digestion and an artificial neural network" R. L. Magaletta et al., Cereal Chemistry vol. 87, no. 4, 2010. For example, soluble fiber can be measured by AOAC Official Methods of Analysis 2011.25. For example, in some embodiments, a DE can be measured using Lane-Eynon titration. In some embodiments, a DE can be determined using osmometry.

A food product can be any appropriate food product that is designed to include one or more of the compositions containing arabinoxylan described herein. A food product can be material that is used for food or drink by humans or animals, chewing gum, or materials used for components thereof (see, e.g., 21 U.S.C. § 321). In some embodiments, a food product can be a food (e.g., a solid food). For example, in some embodiments, a food product can be pie filing, a cookie (e.g., a chocolate chip cookie), a candy (e.g., a taffy chew), a bar (e.g., a cereal bar or a granola bar), a cake, a bread, a cracker, a canned food (e.g., canned soup, canned fruit), or a dairy product (e.g., yogurt, ice cream). In some embodiments, a food product can be a sweetener (e.g., a solid sweetener or a syrup sweetener as described above). In some embodiments, a food product can be a beverage. For example, in some embodiments, a food product can be a juice (e.g., a juice cocktail), a soda, or an energy drink. In some embodiments, a food product can be chewing gum.

A dietary supplement can be any appropriate dietary supplement that is designed to include one or more of the compositions containing arabinoxylan described herein. In some cases, a dietary supplement can include medicinal products, natural health products, nutraceuticals, vitamins, minerals, protein supplements, and the like. A non-limiting example of a dietary supplement is a fiber supplement. In some cases, a fiber supplement provided herein can be in the form of a powder. In some cases, a dietary supplement provided herein can fall under a definition of a dietary supplement by a regulatory agency (e.g., the United States Food and Drug Administration) under an appropriate statute (e.g., 21 U.S.C. § 321).

A pharmaceutical composition can be any appropriate pharmaceutical composition that is designed to include one or more of the compositions containing arabinoxylan described herein. Typically, a pharmaceutical composition is formulated to include at least one active ingredient (e.g., one, two, three, four, five, or more active ingredients such as drugs) in a pharmaceutically effective amount. In some embodiments, a pharmaceutical composition provided herein can be an oral pharmaceutical formulation. Typically, an oral pharmaceutical formulation includes a sweetener.

This document also provides methods of preparing a composition described herein (e.g., an arabinoxylan composition). A composition described herein can be prepared using the methods described herein.

A composition described herein (e.g., an arabinoxylan composition) can, in some cases, be obtained from lignocellulosic biomass. Lignocellulosic biomass can include plant material that is not typically considered suitable for direct human digestion, such as hard or soft wood, plant stems, and stalks. Sources of lignocellulosic biomass that can be used to make a composition provided herein include, without limitation, straw (e.g., wheat straw), corn stover, sugarcane bagasse, hardwoods, softwoods, and combinations thereof. The lignocellulosic biomass can be obtained as a by-product of other industry, such as agriculture, forestry, and energy crops.

In some cases, the methods described herein can include extracting hemicellulose from a lignocellulosic biomass. Extracting hemicellulose from a lignocellulosic biomass can be accomplished by any appropriate method. In some cases, a method described in U.S. Patent Application Publication No. 2018/0119188 or PCT Patent Application Publication No. WO2016/161515, both of which are incorporated by reference in their entirety, can be used to extract hemicellulose from a lignocellulosic biomass.

In some embodiments, a lignocellulosic biomass can be combined with water, and the lignocellulosic biomass can be activated using conditions comprising a first temperature and a first pressure to form an activated cellulose stream (e.g., a first activating step). In some embodiments, a pre-activating step can precede a first activating step. A first activated cellulose stream can be washed to form a washed first activated cellulose stream and a first soluble extract.

An exemplary method that can be used to produce a first soluble extract is shown in FIG. 1. Lignocellulosic biomass 101 can be fed to reactor 103 wherein lignocellulosic biomass 101 is subjected to a first activation step to produce a first activated cellulose stream 104. In the first activation step, lignocellulosic biomass 101 may be treated at an elevated temperature and pressure to produce first activated cellulose stream 104, e.g., comprising cellulose II and insoluble solids. The first activation step can be conducted in the presence of water. Water may be introduced into reactor 103 by one or more of: being present in lignocellulosic biomass 101, being present in reactor 103 when lignocellulosic biomass is introduced into reactor 103, or being introduced by feed stream 102. Reactor 103 can be a batch reactor or a continuous process reactor. In the case of a batch reactor, lignocellulosic biomass 101 can be fed to reactor 103, and the reactor, which can be a stirred tank reactor, can be raised to the operating conditions for a desired time. If reactor 103 is a continuous flow reactor, then it can be a steam exposition reactor and can be maintained at the desired operating condition. First activated cellulose stream 104 can be washed to extract soluble non-cellulosic components such as arabinoxylan and some ash, extractives and lignin. First activated cellulose stream 104 and wash water 106 may be introduced to wash reactor 105 to produce soluble extract 107 and a washed first activated cellulose stream 108. Wash reactor 105 can be any appropriate reactor. Optionally, wash reactor 105 may be operated counter-currently, and it may be a counter-current belt filter. Other filtration or separation methods may be used such as a filter press, twin wire press, twin roll press, rotary vacuum filter, or a centrifuge.

A lignocellulosic biomass can be any appropriate feedstock. For example, the lignocellulosic biomass may comprise one or more of straw, corn stover, bagasse, hardwoods, softwoods, energy crops, and the like. The raw agricultural material that is provided can, in some cases, be treated to remove rocks, soil, or other material present in the raw agricultural material and to reduce the size of the raw agricultural or forest based material that is fed to the process, such as by comminution, grinding, milling or otherwise treated. In some cases, a lignocellulosic biomass used to produce a composition described herein is wheat straw.

In some cases, a pre-activating step can include treating lignocellulosic biomass (e.g., wheat straw) with steam. A pre-activating step can include any appropriate temperature, pressure, and duration. In some embodiments, the temperature of a pre-activating step can be about 110° C. to about 150° C. (e.g., about 110° C. to about 140° C., about 110° C. to about 130° C., about 120° C. ° C. to about 150° C., about 120° C. to about 140° C., or about 125° C. to about 135° C.). In some embodiments, the duration of a pre-activating step can be about 5 minutes to about 30 minutes (e.g., about 5 minutes to about 25 minutes, about 5 minutes to about 15 minutes, about 10 minutes to about 30 minutes, about 20 minutes to about 30 minutes, about 10 minutes to about 30 minutes, or about 13 minutes to about 17 minutes). In some embodiments, the pressure of a pre-activation step can be about 10 psi to about 20 psi (e.g., about 10 to about 15 psi, about 15 to about 20 psi, about 10 psi, about 15 psi, or about 20 psi).

In some cases, a first activation step may be conducted under conditions that increase the amount of cellulose II in the first activated cellulose stream relative to the amount of cellulose II in the feedstock.

The temperature of a first activation step can be any appropriate temperature. In some cases, the temperature of a first activation step can be greater than 190° C. (e.g., greater than 200° C., 210° C., 220° C., 230° C., or 240° C.). In some embodiments, the temperature of a first activation step can be less than about 250° C. (e.g., less than 240° C., 230° C., or 220° C.). In some embodiments, the temperature of a first activation step can be about 190° C. to about 250° C. (e.g., about 190° C. to about 230° C., 190° C. to about 225° C. about 190° C. to about 210° C., about 210° C. to about 250° C., about 230° C. to about 250° C., about 200° C. to about 240° C., about 210° C. to about 230° C., about 215° C. to about 225° C., or about 221° C. to about 223° C.).

The amount of moisture that is introduced in the first activation step can be any appropriate amount. In some embodiments, the amount of moisture can be at least about 30% (e.g., at least about 40% or at least about 50%) on the basis of the lignocellulosic biomass plus the moisture. In some embodiments, the amount of moisture can be less than 90% (e.g., less than 80%, 70%, or 60%). In some embodiments, the amount of moisture in the first activation step can be about 50%. In some embodiments, the amount of moisture in the first activation step can be about 10% to about 65% (e.g., about 10% to about 60%, about 10% to about 50%, about 10% to about 40%, about 10% to about 30%, about 10% to about 20%, about 20% to about 65%, about 30% to about 65%, about 40% to about 65%, about 50% to about 65%, about 20% to about 50%, about 30% to about 60%, or about 35% to about 55%).

The moisture in the first activation step can be in the form of steam or liquid water. It will be appreciated that the temperature and pressure of the first activation step may be selected such that liquid water in the first activation step. It will be appreciated that the temperature and pressure of the first activation step may be selected such that steam is present in the first activation step.

The pressure of a first activation step can be any appropriate pressure. In some embodiments, the pressure can be at least about 200 psig (e.g., at least about 250, 300, or 350 psig). In some embodiments, the pressure can be less than 500 psig (e.g., less than about 450 or 400 psig. Without being bound by any particular theory, it is believed that pressure in a reactor corresponds to temperature as per saturated steam thermodynamics as a minimum. In some embodiments, pressure may be increased over and above that value by adding a pressurized gas, or adding superheat.

The duration of the first activation step can be any appropriate duration. In some embodiments, the first activation step can be less than 30 minutes (e.g., less than 20, 10, or 5 minutes). In some embodiments, the duration of the first activation step can be about 1 minute to about 30 minutes (e.g., about 1 to about 20 min, about 1 to about 15 min, about 1 to about 10 min, about 5 to about 30 min, about 10 to about 30 min, about 20 to about 30 min, about 5 to about 25 min, about 5 to about 15 min, or about 8 to about 12 min). It will be appreciated that duration of the first activation step can vary depending upon many factors including severity of the first activation step, e.g., the temperature and pressure of the first activation step.

It will be appreciated that the temperatures, pressures, and duration of treatment may be combined in any desired combination. Accordingly, for example, the first activation step can include subjecting a lignocellulosic biomass to a pressure between 200 and 500 psig and a temperature between 200 and 250° C. for 1 to 30 minutes, or a pressure between 200 and 500 psig and a temperature between 190 and 215° C. for less than 4 minutes. As another example, a pre-activation step can include subjecting a lignocellulosic biomass to steam treatment for about 13 to about 17 minutes (e.g., about 15 minutes) at a pressure of about 13 to about 17 psi (e.g., about 15 psi) and a temperature of about 125° C. to about 135° C. (e.g., about 130° C.). As yet another example, a first activation step can include subjecting a lignocellulosic biomass (e.g., a lignocellulosic biomass that has undergone a pre-activation step) for about 8 to about 12 minutes (e.g., about 10 minutes) at a pressure of about 300 to about 340 psi (e.g., about 305 to about 335 psi) and a temperature of about 215° C. to about 230° C. (e.g., about 222° C.).

A first activated cellulose stream can have any appropriate solids content. For example, a first activated cellulose stream can have a solids content of between about 30% and 50% solids by weight. In some cases, the solids can be mainly cellulose. In some cases, the solids can include lignin, arabinoxylan, and/or minor components such as ash, protein, or extractives.

A first activated cellulose stream can be washed to form a first washed activated cellulose stream and a first soluble extract. A first activated cellulose stream can be washed with water. The water can include any appropriate solutes. In some embodiments, the wash water can have a temperature of about 40° C. to about 100° C. (e.g., about 40° C. to about 80° C., about 40° C. to about 60° C., about 60° C. to about 100° C., about 80° C. to about 100° C., about 50° C. to about 90° C., about 60° C. to about 80° C., about 70° C. to about 90° C., or about 55° C. to about 65° C.). In some embodiments, the wash water can have a temperature of about 25° C. to about 95° C. (e.g., about 25° C. to about 75° C., about 25° C. to about 50° C., about 50° C. to about 95° C., about 75° C. to about 95° C., about 25° C. to about 50° C., or about 25° C. to about 75° C.).

A first soluble extract can be separated from a washed first activated cellulose stream by any appropriate method. In some embodiments, a first soluble extract can be separated from a washed first cellulose stream by filtration (e.g., vacuum filtration).

A first soluble extract (e.g., including arabinoxylan) can undergo further processing steps in some cases. In some embodiments, first soluble extract can undergo one or more additional steps to form a composition described herein (e.g., an arabinoxylan composition).

Processing can include any appropriate steps. In some embodiments, processing steps can include one or more of: treating with carbon (e.g., activated carbon) or nanofiltering, in any appropriate order. It will be appreciated that other techniques could also be used. In some embodiments, processing can not include treating with carbon (e.g., activated carbon).

Carbon treatment can include treating a first soluble extract (or a first soluble extract that has undergone one or more processing steps) with carbon (e.g., activated carbon). The loading of carbon can be any appropriate loading. For example, the carbon (e.g., activated carbon) can be used in a loading of about 0.05% to about 0.3% (e.g., 0.05% to about 0.2%, about 0.05% to about 0.1%, about 0.1% to about 0.3%, about 0.1% to about 0.2%, or about 0.05% to about 0.15%) by dry weight of one or more components in the composition (e.g., arabinoxylan). Without being bound by any particular theory, it is believed that a loading of about 0.1% or less (e.g., less than about 0.09%, 0.08%, 0.07%, or 0.06%) by dry weight of one or more components in the composition (e.g., arabinoxylan) can increase the yield of arabinoxylan by minimizing the amount of arabinoxylan adsorbed by the carbon.

Nanofiltering (e.g., of a first soluble extract or a first soluble extract that has undergone one or more processing steps) can include any appropriate conditions. In some cases, nanofiltering can use a filter with a pore size of about 0.01 to about 10 nm (e.g., about 0.01 to about 0.05 nm, about 0.04 to about 0.05 nm, about 0.05 to about 0.1 nm, about 0.1 to about 0.5 nm, about 0.5 to about 1 nm, about 1 to about 5 nm, or about 5 to about 10 nm). In some cases, nanofiltering can use a filter with a pore size of about 1 to about 10 nm (e.g., about 1 to about 5 nm or about 5 to about 10 nm). Without being bound by any particular theory, it is believed that nanofiltration can remove low molecular weight impurities, ions, and/or water and concentrate the composition, and that removal of protein can help to decrease foaming in a composition as described herein. In some embodiments, depending on the pore size, nanofiltering can be used to decrease the amount of protein in a composition described herein. For example, in some embodiments, nanofiltering can use a filter with a molecular weight cutoff (MWCO) of about 100 Da to about 250 kDa (e.g., about 100 Da to about 500 Da, about 100 Da to about 1 kDa, about 1 kDa to about 3 kDa, about 1 kDa to about 10 kDa, about 10 kDa to about 30 kDa, about 10 kDa to about 50 kDa, about 50 kDa to about 100 kDa, or about 100 kDa to about 250 kDa). In some embodiments, nanofiltering can include two filtration steps, using differently sized pores (e.g., a larger pore size, and then a smaller pore size), such as any of the pore sizes described herein. For example, a first filtration can be performed using a filter with a MWCO of about 100 kDa to about 250 kDa (e.g., about 100 kDa to about 200 kDa or about 150 kDa to about 250 kDa). For example, a second filtration can be performed using a filter with a MWCO of about 100 Da to about 30 kDa (e.g., about 100 Da to about 500 Da, about 100 Da to about 1 kDa, about 1 kDa to about 5 kDa, about 1 kDa to about 10 kDa, about 5 kDa to about 15 kDa, about 10 kDa to about 30 kDa, or about 15 kDa to about 30 kDa). In some embodiments, a retentate, or filtration solids (e.g., comprising one or more proteins), can be retained for further purification or another use. Accordingly, provided herein is a retentate or filtration solids (e.g., comprising one or more proteins) produced by the methods described herein.

In some embodiments, a first soluble extract can be processed by, sequentially, carbon treatment and nanofiltration to form a composition.

In some embodiments, a first soluble extract can be processed by nanofiltration to form a composition.

In some cases, a composition containing arabinoxylan can be prepared by other methods as well. For example, a composition containing high molecular weight arabinoxylan can be obtained from a commercial supplier. The composition containing high molecular weight arabinoxylan can, in some cases, have an alkaline pH. In some embodiments, the arabinoxylan of a composition containing high molecular weight arabinoxylan can have a molecular weight ($M_w$) of at least about 20 kDa (e.g., at least about 30, 50, 75, or 100 kDa). In some embodiments, the high molecular weight arabinoxylan can have a molecular weight ($M_w$) of about 20 kDa to about 300 kDa (e.g., about 20 to about 250 kDa, about 20 to about 200 kDa, about 20 to about 150 kDa, about 20 to about 100 kDa, about 20 to about 50 kDa, about 50 to about 300 kDa, about 100 to about 300 kDa, about 150 to about 300 kDa, about 200 to about 200 kDa, about 250 to about 300 kDa, or about 100 to about 200 kDa).

A composition containing high molecular weight arabinoxylan can be treated to reduce the molecular weight ($M_w$) to form a reduced-mass arabinoxylan. In some embodiments, alkaline conditions can be used to reduce the molecular weight of high molecular weight arabinoxylan. In some embodiments, alkaline conditions can include a pH of 9.5 to about 11.5 (e.g., about 9.5 to about 11.0, about 9.5 to about 10.5, about 9.5 to about 10.0, about 10.0 to about 11.5, about 10.0 to about 11.0, about 10.0 to about 10.5, about 10.5 to about 11.5, about 10.5 to about 11.0, about 11.0 to about 11.5, about 9.5, about 10.0, about 10.5, about 11.0, or about 11.5). Without being bound by any particular theory, it is believed that a reduction in molecular weight is related to the pH, duration, temperature, and pressure of treatment. In some embodiments, the pressure can be atmospheric pressure. In some embodiments, the duration of alkaline treatment can be about 30 minutes to about 8 hours (e.g., about 30 minutes to about 6 hours, about 30 minutes to about 4 hours, about 30 minutes to about 2 hours, about 30 minutes to about 1 hour, about 1 hour to about 8 hours, about 2 hours to about 8 hours, about 4 hours to about 8 hours, about 1 hour to about 6 hours, or about 2 hours to about 4 hours). In some embodiments, the temperature can be about 60° C. to about 150° C. (e.g., about 60° C. to about 120° C., about 60° C. to about 100° C., about 60° C. to about 80° C., about 70° C. to about 150° C., about 90° C. to about 150° C., about 110° C. to about 150° C., about 130° C. to about 150° C., about 80° C. to about 130° C., or about 100° C. to about 110° C.). The alkaline treatment can reduce the molecular weight to a desired molecular weight, depending on the conditions. In some embodiments, the molecular weight ($M_w$) of the alkaline-treated arabinoxylan can be about 5500 to about 6000 Da (e.g., about 5500 to about 5900 Da, about 5500 to about 5700 Da, about 5600 to about 6000 Da, about 5700 to about 6000 Da, or about 5700 to about 5900 Da).

A reduced-mass arabinoxylan can be processed using any appropriate steps to form a composition described herein (e.g., an arabinoxylan composition). In some embodiments, a reduced-mass arabinoxylan composition can be processed using any of the steps as described herein to from a composition described herein. In some embodiments, a reduced-mass arabinoxylan can undergo treating with carbon (e.g., activated carbon) or nanofiltering, in any appropriate order, to form a composition (e.g., an arabinoxylan composition). In some embodiments, a composition made from a reduced-mass arabinoxylan can be used in any of the applications (e.g., in a sweetener, in a food product, in a pharmaceutical composition, or in a dietary supplement) described herein.

In some embodiments, a reduced-mass arabinoxylan can be combined with a first soluble extract, in any appropriate ratio. For example, about 25% to about 75% (e.g., about 25% to about 50%, about 50% to about 75%, about 25%, about 50%, or about 75%) by dry weight of reduced-mass arabinoxylan can be combined with about 25% to about 75% (e.g., about 25% to about 50%, about 50% to about 75%, about 25%, about 50%, or about 75%) by dry weight of a first soluble extract. Such a combination, in some embodiments, can undergo treating with carbon (e.g., activated carbon), or nanofiltering, in any appropriate order, to form a composition.

A composition described herein (e.g., an arabinoxylan composition) can be dried (e.g., partially or fully dried). A composition can be dried using any appropriate method. For example, in some embodiments, a composition described herein (e.g., an arabinoxylan composition) can be dried using spray drying, mat drying, or freeze drying.

Concentration of the composition (e.g., an arabinoxylan composition) can be carried out, for example, by evaporation or reverse osmosis. Reverse osmosis can also be used to pre-concentrate the arabinoxylan followed by evaporation. Any appropriate concentration method and any appropriate drying method can be used. A non-limiting example of an evaporation method to preserve taste and/or color is falling film evaporation under vacuum. Other non-limiting examples drying methods that can preserve taste and/or color are freeze drying or spray drying.

EXEMPLARY EMBODIMENTS

Embodiment 1 is a composition comprising:
about 80% to about 99% by dry weight of arabinoxylan, wherein the arabinoxylan has a molecular weight ($M_w$) of about 3100 Da to about 8400 Da.

Embodiment 2 is a composition comprising:
about 80% to about 99% by dry weight of arabinoxylan, wherein the arabinoxylan has a molecular weight ($M_w$) of at least about 4800 Da.

Embodiment 3 is a composition comprising:
about 80% to about 99% by dry weight of arabinoxylan, wherein the arabinoxylan comprises about 5% to about 40% by dry weight of arabinose units.

Embodiment 4 is a composition comprising:
about 80% to about 99% by dry weight of arabinoxylan, wherein the arabinoxylan comprises about 60% to about 85% by dry weight of xylose units.

Embodiment 5 is a composition comprising:
about 80% to about 99% by dry weight of arabinoxylan, wherein the arabinoxylan comprises about 12% to about 14% by dry weight of glucose units.

Embodiment 6 is a composition comprising:
about 80% to about 99% by dry weight of arabinoxylan, wherein the arabinoxylan comprises about 2% to about 6% by dry weight of galactose units.

Embodiment 7 is a composition comprising:
about 80% to about 99% by dry weight of arabinoxylan, wherein the arabinoxylan comprises less than about 1% by dry weight of mannose units.

Embodiment 8 is a composition comprising:
about 80% to about 99% by dry weight of arabinoxylan, wherein the arabinoxylan comprises arabinose units and xylose units, and a molar ratio of the arabinose units and xylose units is about 0.05 to about 0.65.

Embodiment 9 is a composition comprising:
about 80% to about 99% by dry weight of arabinoxylan, wherein the arabinoxylan comprises glucose units and xylose units, and a molar ratio of the glucose units and xylose units is about 0.10 to about 0.25.

Embodiment 10 is a composition comprising:
about 80% to about 99% by dry weight of arabinoxylan; and
about 1% to about 14% by dry weight of one or more polyphenols.

Embodiment 11 is the composition of any one of embodiments 1-10, comprising about 88% to about 99% by dry weight of arabinoxylan.

Embodiment 12 is the composition of any one of embodiments 1-11, comprising about 90% to about 99% by dry weight of arabinoxylan.

Embodiment 13 is a composition comprising:
about 80% to about 96% by dry weight of arabinoxylan; and
about 4% to about 20% by dry weight of carbohydrate polymers other than arabinoxylan, sugar monomers, protein, and ash.

Embodiment 14 is a composition comprising:
about 80% to about 95% by dry weight of arabinoxylan;
about 4% to about 20% by dry weight of carbohydrate polymers other than arabinoxylan, sugar monomers, protein, and ash; and
about 1% to about 14% by dry weight of one or more polyphenols.

Embodiment 15 is the composition of any one of embodiments 1-12, comprising about 88% to about 90% by dry weight of arabinoxylan.

Embodiment 16 is the composition of any one of embodiments 1-13, comprising about 90% to about 95% by dry weight of arabinoxylan.

Embodiment 17 is the composition of any one of embodiments 1-14, comprising about 91% to about 93% by dry weight of arabinoxylan.

Embodiment 18 is the composition of any one of embodiments 1-12 or 15-17, comprising about 4% to about 20% by dry weight of carbohydrate polymers other than arabinoxylan, sugar monomers, protein, ash, or a combination thereof.

Embodiment 19 is the composition of any one of embodiments 1-18, comprising about 4% to about 12% by dry weight of carbohydrate polymers other than arabinoxylan, sugar monomers, protein, ash, or a combination thereof.

Embodiment 20 is the composition of any one of embodiments 1-12 or 15-19, comprising about 6% to about 10% by dry weight of carbohydrate polymers other than arabinoxylan, sugar monomers, protein, ash, or a combination thereof.

Embodiment 21 is the composition of any one of embodiments 1-12 or 15-20, comprising about 5% to about 7% by dry weight of carbohydrate polymers other than arabinoxylan, sugar monomers, protein, ash, or a combination thereof.

Embodiment 22 is the composition of any one of embodiments 1-12 or 15-19, comprising about 8% to about 10% by dry weight of carbohydrate polymers other than arabinoxylan, sugar monomers, protein, ash, or a combination thereof.

Embodiment 23 is the composition of any one of embodiments 1-9, 11-13, or 15-22, comprising about 1% to about 14% by dry weight of one or more polyphenols.

Embodiment 24 is the composition of any one of embodiments 1-23, comprising about 1% to about 12% by dry weight of one or more polyphenols.

Embodiment 25 is the composition of any one of embodiments 1-24, comprising about 2% to about 5% by dry weight of one or more polyphenols.

Embodiment 26 is the composition of any one of embodiments 1-25, comprising about 5% to about 10% by dry weight of one or more polyphenols.

Embodiment 27 is the composition of any one of embodiments 1-26, comprising about 1% to about 3% by dry weight of one or more polyphenols.

Embodiment 28 is the composition of any one of embodiments 1-27, comprising about 1% to about 2% by dry weight of one or more polyphenols.

Embodiment 29 is the composition of any one of embodiments 1-2 or 4-28, wherein the arabinoxylan comprises about 5% to about 40% by dry weight of arabinose units.

Embodiment 30 is the composition of any one of embodiments 1-29, wherein the arabinoxylan comprises about 5% to about 25% by dry weight of arabinose units.

Embodiment 31 is the composition of any one of embodiments 1-30, wherein the arabinoxylan comprises about 5% to about 15% by dry weight of arabinose units.

Embodiment 32 is the composition of any one of embodiments 1-30, wherein the arabinoxylan comprises about 10% to about 20% by dry weight of arabinose units.

Embodiment 33 is the composition of any one of embodiments 1-30, wherein the arabinoxylan comprises about 15% to about 25% by dry weight of arabinose units.

Embodiment 34 is the composition of any one of embodiments 1-31, wherein the arabinoxylan comprises about 5% to about 7% by dry weight of arabinose units.

Embodiment 35 is the composition of any one of embodiments 1-30, wherein the arabinoxylan comprises about 18% to about 20% by dry weight of arabinose units.

Embodiment 36 is the composition of any one of embodiments 1-3 or 5-35, wherein the arabinoxylan comprises about 60% to about 85% by dry weight of xylose units.

Embodiment 37 is the composition of any one of embodiments 1-36, wherein the arabinoxylan comprises about 60% to about 70% by dry weight of xylose units.

Embodiment 38 is the composition of any one of embodiments 1-36, wherein the arabinoxylan comprises about 70% to about 80% by dry weight of xylose units.

Embodiment 39 is the composition of any one of embodiments 1-36, wherein the arabinoxylan comprises about 75% to about 85% by dry weight of xylose units.

Embodiment 40 is the composition of any one of embodiments 1-37, wherein the arabinoxylan comprises about 62% to about 66% by dry weight of xylose units.

Embodiment 41 is the composition of any one of embodiments 1-36, wherein the arabinoxylan comprises about 78% to about 82% by dry weight of xylose units.

Embodiment 42 is the composition of any one of embodiments 1-4 or 6-41, wherein the arabinoxylan comprises about 8% to about 15% by dry weight of glucose units.

Embodiment 43 is the composition of any one of embodiments 1-42, wherein the arabinoxylan comprises about 10% to about 15% by dry weight of glucose units.

Embodiment 44 is the composition of any one of embodiments 1-42, wherein the arabinoxylan comprises about 9% to about 11% by dry weight of glucose units.

Embodiment 45 is the composition of any one of embodiments 1-42, wherein the arabinoxylan comprises about 12% to about 14% by dry weight of glucose units.

Embodiment 46 is the composition of any one of embodiments 1-5 or 7-45, wherein the arabinoxylan comprises about 2% to about 6% by dry weight of galactose units.

Embodiment 47 is the composition of any one of embodiments 1-46, wherein the arabinoxylan comprises about 3% to about 5% by dry weight of galactose units.

Embodiment 48 is the composition of any one of embodiments 1-6 or 8-47, wherein the arabinoxylan comprises less than about 1% by dry weight of mannose units.

Embodiment 49 is the composition of any one of embodiments 1-48, wherein the arabinoxylan comprises less than about 0.5% by dry weight of mannose units.

Embodiment 50 is the composition of any one of embodiments 1-7 or 9-49, wherein the arabinoxylan comprises arabinose units and xylose units, and a molar ratio of the arabinose units and xylose units is about 0.05 to about 0.65.

Embodiment 51 is the composition of any one of embodiments 1-50, wherein the arabinoxylan comprises arabinose units and xylose units, and a molar ratio of the arabinose units and xylose units is about 0.05 to about 0.35.

Embodiment 52 is the composition of any one of embodiments 1-51, wherein the arabinoxylan comprises arabinose units and xylose units, and a molar ratio of the arabinose units and xylose units is about 0.05 to about 0.15.

Embodiment 53 is the composition of any one of embodiments 1-51, wherein the arabinoxylan comprises arabinose units and xylose units, and a molar ratio of the arabinose units and xylose units is about 0.15 to about 0.25.

Embodiment 54 is the composition of any one of embodiments 1-51, wherein the arabinoxylan comprises arabinose units and xylose units, and a molar ratio of the arabinose units and xylose units is about 0.25 to about 0.35.

Embodiment 55 is the composition of any one of embodiments 1-51, wherein the arabinoxylan comprises arabinose units and xylose units, and a molar ratio of the arabinose units and xylose units is about 0.06 to about 0.10.

Embodiment 56 is the composition of any one of embodiments 1-51, wherein the arabinoxylan comprises arabinose units and xylose units, and a molar ratio of the arabinose units and xylose units is about 0.28 to about 0.32.

Embodiment 57 is the composition of any one of embodiments 1-8 or 10-56, wherein the arabinoxylan comprises glucose units and xylose units, and a molar ratio of the glucose units and xylose units is about 0.10 to about 0.25.

Embodiment 58 is the composition of any one of embodiments 1-57, wherein the arabinoxylan comprises glucose units and xylose units, and a molar ratio of the glucose units and xylose units is about 0.15 to about 0.25.

Embodiment 59 is the composition of any one of embodiments 1-57, wherein the arabinoxylan comprises glucose units and xylose units, and a molar ratio of the glucose units and xylose units is about 0.10 to about 0.20.

Embodiment 60 is the composition of any one of embodiments 1-57, wherein the arabinoxylan comprises glucose units and xylose units, and a molar ratio of the glucose units and xylose units is about 0.11 to about 0.15.

Embodiment 61 is the composition of any one of embodiments 1-57, wherein the arabinoxylan comprises glucose units and xylose units, and a molar ratio of the glucose units and xylose units is about 0.18 to about 0.22.

Embodiment 62 is the composition of any one of embodiments 1-61, wherein the composition comprises less than about 1% by dry weight of carbohydrate polymers other than arabinoxylan.

Embodiment 63 is the composition of any one of embodiments 1-62, wherein the composition comprises less than about 0.5% by dry weight of carbohydrate polymers other than arabinoxylan.

Embodiment 64 is the composition of any one of embodiments 1-63, wherein the composition comprises about 0.5% to about 5% by dry weight of protein.

Embodiment 65 is the composition of any one of embodiments 1-64, wherein the composition comprises about 1% to about 4% by dry weight of protein.

Embodiment 66 is the composition of any one of embodiments 1-64, wherein the composition comprises about 0.8% to about 1.2% by dry weight of protein.

Embodiment 67 is the composition of any one of embodiments 1-65, wherein the composition comprises about 3.6% to about 4% by dry weight of protein.

Embodiment 68 is the composition of any one of embodiments 1-67, wherein the composition comprises about 0.5% to about 6% by dry weight of ash.

Embodiment 69 is the composition of any one of embodiments 1-68, wherein the composition comprises about 1% to about 5% by dry weight of ash.

Embodiment 70 is the composition of any one of embodiments 1-69, wherein the composition comprises about 1% to about 3% by dry weight of ash.

Embodiment 71 is the composition of any one of embodiments 1-68, wherein the composition comprises about 0.8% to about 1.2% by dry weight of ash.

Embodiment 72 is the composition of any one of embodiments 1-68, wherein the composition comprises about 4.5% to about 4.9% by dry weight of ash.

Embodiment 73 is the composition of any one of embodiments 3-72, wherein the arabinoxylan has a molecular weight ($M_w$) of about 3100-8400 Da.

Embodiment 74 is the composition of any one of embodiments 1 or 3-73, wherein the arabinoxylan has a molecular weight of at least 4800 Da.

Embodiment 75 is the composition of any one of embodiments 1-74, wherein the composition has a molecular weight ($M_w$) of about 5500-6000 Da.

Embodiment 76 is the composition of any one of embodiments 1-75, wherein the composition has a molecular weight ($M_w$) of about 5500-5700 Da.

Embodiment 77 is the composition of any one of embodiments 1-76, wherein the composition has a molecular weight ($M_w$) of about 5600-5800 Da.

Embodiment 78 is the composition of any one of embodiments 1-77, wherein the composition has a molecular weight ($M_n$) of about 3000-3500 Da.

Embodiment 79 is the composition of any one of embodiments 1-78, wherein the composition has a molecular weight ($M_n$) of about 3200-3400 Da.

Embodiment 80 is the composition of any one of embodiments 10-12 or 14-79, wherein the one or more polyphenols comprise units selected from the group consisting of ferulic acid, gallic acid, 4-hydroxybenzoic acid, coumaric acid, syringic acid, sinapic acid, rosemarinic acid, vanillin, and combinations thereof.

Embodiment 81 is the composition of any one of embodiments 10-12 or 14-80, wherein the composition comprises about 0.001% to about 0.005% by dry weight of ferulic acid units.

Embodiment 82 is the composition of any one of embodiments 10-12 or 14-81, wherein the composition comprises about 0.001% to about 0.003% by dry weight of ferulic acid units.

Embodiment 83 is the composition of any one of embodiments 10-12 or 14-82, wherein the composition comprises about 0.01% to about 0.05% by dry weight of gallic acid units.

Embodiment 84 is the composition of any one of embodiments 10-12 or 14-83, wherein the composition comprises about 0.01% to about 0.03% by dry weight of gallic acid units.

Embodiment 85 is the composition of any one of embodiments 10-12 or 14-84, wherein the composition comprises about 1% to about 2% by dry weight of 4-hydroxybenzoic acid units.

Embodiment 86 is the composition of any one of embodiments 10-12 or 14-85, wherein the composition comprises about 1.0% to about 1.5% by dry weight of 4-hydroxybenzoic acid units.

Embodiment 87 is the composition of any one of embodiments 10-12 or 14-86, wherein the composition comprises about 0.01% to about 0.05% by dry weight of coumaric acid units.

Embodiment 88 is the composition of any one of embodiments 10-12 or 14-87, wherein the composition comprises about 0.01% to about 0.03% by dry weight of coumaric acid units.

Embodiment 89 is the composition of any one of embodiments 10-12 or 14-88, wherein the composition comprises about 0.05% to about 0.1% by dry weight of syringic acid units.

Embodiment 90 is the composition of any one of embodiments 10-12 or 14-89, wherein the composition comprises about 0.05% to about 0.07% by dry weight of syringic acid units.

Embodiment 91 is the composition of any one of embodiments 10-12 or 14-90, wherein the composition comprises about 0.1% to about 0.5% by dry weight of synapic acid units.

Embodiment 92 is the composition of any one of embodiments 10-12 or 14-91, wherein the composition comprises about 0.3% to about 0.5% by dry weight of synapic acid units.

Embodiment 93 is the composition of any one of embodiments 10-12 or 14-92, wherein the composition comprises about 0.05% to about 0.3% by dry weight of rosemarinic acid units.

Embodiment 94 is the composition of any one of embodiments 10-12 or 14-93, wherein the composition comprises about 0.1% to about 0.2% by dry weight of rosemarinic acid units.

Embodiment 95 is the composition of any one of embodiments 10-12 or 14-94, wherein the composition comprises about 0.001% to about 0.01% by dry weight of vanillin units.

Embodiment 96 is the composition of any one of embodiments 10-12 or 14-95, wherein the composition comprises about 0.004% to about 0.006% by dry weight of vanillin units.

Embodiment 97 is the composition of any one of embodiments 1-96, wherein the composition is light brown.

Embodiment 98 is the composition of any one of embodiments 1-97, wherein the composition has an antioxidant level of about 25000 to about 50000 μmol TE/100 g.

Embodiment 99 is the composition of any one of embodiments 1-98, wherein the composition has an antioxidant level of about 25000 to about 35000 μmol TE/100 g.

Embodiment 100 is the composition of any one of embodiments 1-99, wherein the composition comprises epigallocatechin gallate.

Embodiment 101 is a composition comprising:
  about 88% to about 90% by dry weight of arabinoxylan, wherein the arabinoxylan comprises:
    about 5% to about 7% by dry weight of arabinose units;
    about 78% to about 82% by dry weight of xylose units;
    about 9% to about 11% by dry weight of glucose units;
    about 3% to about 4% by dry weight of galactose units;
  about 4% to about 6% of carbohydrate polymers that are not arabinoxylan, sugar monomers, protein, ash, or a combination thereof; and
  about 3% to about 11% by dry weight of one or more polyphenols,
  wherein the molecular weight ($M_w$) of the composition is about 5400 to about 5800 Da.

Embodiment 102 is a composition comprising:
  about 90% to about 94% by dry weight of arabinoxylan, wherein the arabinoxylan comprises:
    about 17% to about 21% by dry weight of arabinose units;
    about 62% to about 66% by dry weight of xylose units;
    about 12% to about 14% by dry weight of glucose units;
    about 3% to about 4% by dry weight of galactose units;
  about 8% to about 11% of carbohydrate polymers that are not arabinoxylan, sugar monomers, protein, ash, or a combination thereof; and
  about 1% to about 3% by dry weight of one or more polyphenols,
  wherein the molecular weight ($M_w$) of the composition is about 5600 to about 6000 Da.

Embodiment 103 is the composition of any one of embodiments 101-102, wherein the molecular weight ($M_n$) of the composition is about 3100 to about 3500 Da.

Embodiment 104 is the composition any one of embodiments 101-103, wherein the composition comprises about 0.001% to about 0.003% by dry weight of ferulic acid units.

Embodiment 105 is the composition of any one of embodiments 101-104, wherein the composition comprises about 0.01% to about 0.02% by dry weight of gallic acid units.

Embodiment 106 is the composition of any one of embodiments 101-105, wherein the composition comprises about 1.0% to about 1.5% by dry weight of 4-hydroxybenzoic acid units.

Embodiment 107 is the composition of any one of embodiments 101-106, wherein the composition comprises about 0.01% to about 0.02% by dry weight of coumaric acid units.

Embodiment 108 is the composition of any one of embodiments 101-107, wherein the composition comprises about 0.05% to about 0.07% by dry weight of syringic acid units.

Embodiment 109 is the composition of any one of embodiments 101-108, wherein the composition comprises about 0.3% to about 0.5% by dry weight of sinapic acid units.

Embodiment 110 is the composition of any one of embodiments 101-109, wherein the composition comprises about 0.1% to about 0.2% by dry weight of rosemarinic acid units.

Embodiment 111 is the composition of any one of embodiments 101-110, wherein the composition comprises about 0.004% to about 0.006% by dry weight of vanillin units.

Embodiment 112 is the composition of any one of embodiments 101-111, wherein the composition has an antioxidant level of about 27000 to about 31000 μmol TE/100 g.

Embodiment 113 is the composition of any one of embodiments 101-112, wherein the composition comprises epigallocatechin gallate.

Embodiment 114 is a food product comprising the composition of any one of embodiments 1-113.

Embodiment 115 is a dietary supplement comprising the composition of any one of embodiments 1-113.

Embodiment 116 is a pharmaceutical composition comprising the composition of any one of embodiments 1-113.

Embodiment 117 is the food product of embodiment 114, the dietary supplement of embodiment 115, or the pharmaceutical composition of embodiment 116, wherein the composition of any one of embodiments 1-113 is present in an amount of at least 7 g per serving.

Embodiment 118 is the food product of embodiment 114, the dietary supplement of embodiment 115, or the pharmaceutical composition of embodiment 116, wherein the composition of any one of embodiments 1-113 is present in an amount of at least 10 g per serving.

Embodiment 119 is the food product of embodiment 114, the dietary supplement of embodiment 115, or the pharmaceutical composition of embodiment 116, wherein the composition of any one of embodiments 1-113 is present in an amount of at least 12 g per serving.

Embodiment 120 is the food product of embodiment 114, the dietary supplement of embodiment 115, or the pharmaceutical composition of embodiment 116, wherein the composition of any one of embodiments 1-113 is present in an amount of at least 14 g per serving.

Embodiment 121 is use of a composition of any one of embodiments 1-113 in a food product.

Embodiment 122 is use of a composition of any one of embodiments 1-113 in a dietary supplement.

Embodiment 123 is use of a composition of any one of embodiments 1-113 in a pharmaceutical composition.

Embodiment 124 is the use of any one of embodiments 121-123, wherein the composition of any one of embodiments 1-113 is present in an amount of at least 7 g per serving.

Embodiment 125 is the use of any one of embodiments 121-123, wherein the composition of any one of embodiments 1-113 is present in an amount of at least 10 g per serving.

Embodiment 126 is the use of any one of embodiments 121-123, wherein the composition of any one of embodiments 1-113 is present in an amount of at least 12 g per serving.

Embodiment 127 is the use of any one of embodiments 121-123, wherein the composition of any one of embodiments 1-113 is present in an amount of at least 14 g per serving.

Embodiment 128 is a method of preparing a composition comprising:
  providing a lignocellulosic biomass;
  combining the lignocellulosic biomass with water;
  activating the lignocellulosic biomass and water using conditions comprising a first temperature and a first pressure to form a first activated cellulose stream;
  washing the first activated cellulose stream to form a washed first activated cellulose stream and a first soluble extract, wherein the first soluble extract comprises arabinoxylan; and
  processing the first soluble extract to form a composition.

Embodiment 129 is the method of embodiment 128, wherein the first temperature is about 190° C. to about 225° C.

Embodiment 130 is the method of embodiment 128 or embodiment 129, wherein the first pressure is about 200 to about 500 psig.

Embodiment 131 is the method of any one of embodiments 128-130, wherein the activating step has a duration of about 1 to about 30 minutes.

Embodiment 132 is the method of any one of embodiments 128-131, wherein washing comprises washing with water at a temperature of about 40° C. and about 100° C.

Embodiment 133 is the method of any one of embodiments 128-132, wherein processing comprises one or more of treating with carbon, nanofiltering, or a combination thereof.

Embodiment 134 is the method of embodiment 133, wherein treating with carbon is treating with activated carbon.

Embodiment 135 is the method of embodiment 133 or embodiment 134, wherein treating with carbon comprises using carbon in an amount of about 0.05% to about 0.15% by dry weight of the arabinoxylan in the first soluble extract.

Embodiment 136 is the method of any one of embodiments 128-135, wherein processing comprises, sequentially, treating with carbon and nanofiltering to form the composition.

Embodiment 137 is the method of any one of embodiments 133-136, wherein nanofiltering comprises filtration using a pore size of about 0.01 to about 10 nm.

Embodiment 138 is the method of embodiment 137, wherein nanofiltering comprises filtration using a pore size of about 0.04 to about 0.05 nm.

Embodiment 139 is the method of embodiment 137, wherein nanofiltering comprises filtration using a pore size of about 1 to about 10 nm.

Embodiment 140 is the method of any one of embodiments 137-139, wherein processing does not comprise treating with carbon.

Embodiment 141 is the method of any one of embodiments 128-140, further comprising, prior to processing, adding a reduced-mass arabinoxylan to the first soluble extract.

Embodiment 142 is the method of embodiment any one of embodiments 128-141, further comprising drying the composition.

Embodiment 143 is the method of any one of embodiments 128-142, wherein the composition comprises:
about 80% to about 99% by dry weight of arabinoxylan, wherein the arabinoxylan has a molecular weight ($M_w$) of about 3100 Da to about 8400 Da.

Embodiment 144 is the method of any one of embodiments 128-142, wherein the composition comprises:
about 80% to about 99% by dry weight of arabinoxylan, wherein the arabinoxylan has a molecular weight ($M_w$) of at least about 4800 Da.

Embodiment 145 is the method of any one of embodiments 128-142, wherein the composition comprises:
about 80% to about 99% by dry weight of arabinoxylan, wherein the arabinoxylan comprises about 5% to about 25% by dry weight of arabinose units.

Embodiment 146 is the method of any one of embodiments 128-142, wherein the composition comprises:
about 80% to about 99% by dry weight of arabinoxylan, wherein the arabinoxylan comprises about 60% to about 85% by dry weight of xylose units.

Embodiment 147 is the method of any one of embodiments 128-142, wherein the composition comprises:
about 80% to about 99% by dry weight of arabinoxylan, wherein the arabinoxylan comprises about 12% to about 14% by dry weight of glucose units.

Embodiment 148 is the method of any one of embodiments 128-142, wherein the composition comprises:
about 80% to about 99% by dry weight of arabinoxylan, wherein the arabinoxylan comprises about 2% to about 6% by dry weight of galactose units.

Embodiment 149 is the method of any one of embodiments 128-142, wherein the composition comprises:
about 80% to about 99% by dry weight of arabinoxylan, wherein the arabinoxylan comprises less than about 1% by dry weight of mannose units.

Embodiment 150 is the method of any one of embodiments 128-142, wherein the composition comprises:
about 80% to about 99% by dry weight of arabinoxylan, wherein the arabinoxylan comprises arabinose units and xylose units, and a molar ratio of the arabinose units and xylose units is about 0.05 to about 0.65.

Embodiment 151 is the method of any one of embodiments 128-142, wherein the composition comprises:
about 80% to about 99% by dry weight of arabinoxylan, wherein the arabinoxylan comprises glucose units and xylose units, and a molar ratio of the glucose units and xylose units is about 0.10 to about 0.25.

Embodiment 152 is the method of any one of embodiments 128-142, wherein the composition comprises:
about 80% to about 99% by dry weight of arabinoxylan; and
about 1% to about 14% by dry weight of one or more polyphenols.

Embodiment 153 is the method of any one of embodiments 143-152, wherein the composition comprises about 88% to about 99% by dry weight of arabinoxylan.

Embodiment 154 is the method of any one of embodiments 143-152, wherein the composition comprises about 90% to about 99% by dry weight of arabinoxylan.

Embodiment 155 is the method of any one of embodiments 128-152, wherein the composition comprises:
about 80% to about 96% by dry weight of arabinoxylan; and
about 4% to about 20% by dry weight of carbohydrate polymers other than arabinoxylan, sugar monomers, protein, and ash.

Embodiment 156 is the method of any one of embodiments 128-155, wherein the composition comprises:
about 80% to about 95% by dry weight of arabinoxylan;
about 4% to about 20% by dry weight of carbohydrate polymers other than arabinoxylan, sugar monomers, protein, ash, or a combination thereof; and
about 1% to about 14% by dry weight of one or more polyphenols.

Embodiment 157 is the method of any one of embodiments 143-156, wherein the composition comprises about 88% to about 90% by dry weight of arabinoxylan.

Embodiment 158 is the method of any one of embodiments 143-157, wherein the composition comprises about 90% to about 95% by dry weight of arabinoxylan.

Embodiment 159 is the method of any one of embodiments 143-158, wherein the composition comprises about 91% to about 93% by dry weight of arabinoxylan.

Embodiment 160 is the method of any one of embodiments 143-154 or 156-159, wherein the composition comprises about 4% to about 20% by dry weight of carbohydrate polymers other than arabinoxylan, sugar monomers, protein, ash, or a combination thereof.

Embodiment 161 is the method of any one of embodiments 143-160, wherein the composition comprises about 4% to about 12% by dry weight of carbohydrate polymers other than arabinoxylan, sugar monomers, protein, ash, or a combination thereof.

Embodiment 162 is the method of any one of embodiments 143-161, wherein the composition comprises about 6% to about 10% by dry weight of carbohydrate polymers other than arabinoxylan, sugar monomers, protein, ash, or a combination thereof.

Embodiment 163 is the method of any one of embodiments 143-162, wherein the composition comprises about 5% to about 7% by dry weight of carbohydrate polymers other than arabinoxylan, sugar monomers, protein, ash, or a combination thereof.

Embodiment 164 is the method of any one of embodiments 143-162, wherein the composition comprises about 8% to about 10% by dry weight of carbohydrate polymers other than arabinoxylan, sugar monomers, protein, ash, or a combination thereof.

Embodiment 165 is the method of any one of embodiments 143-151, 153-155, or 157-164, wherein the composition comprises about 1% to about 14% by dry weight of one or more polyphenols.

Embodiment 166 is the method of any one of embodiments 143-165, wherein the composition comprises about 1% to about 12% by dry weight of one or more polyphenols.

Embodiment 167 is the method of any one of embodiments 143-166, wherein the composition comprises about 2% to about 5% by dry weight of one or more polyphenols.

Embodiment 168 is the method of any one of embodiments 143-167, wherein the composition comprises about 5% to about 10% by dry weight of one or more polyphenols.

Embodiment 169 is the method of any one of embodiments 143-168, wherein the composition comprises about 1% to about 3% by dry weight of one or more polyphenols.

Embodiment 170 is the method of any one of embodiments 143-169, wherein the composition comprises about 1% to about 2% by dry weight of one or more polyphenols.

Embodiment 171 is the method of any one of embodiments 143-144 or 146-170, wherein the arabinoxylan comprises about 5% to about 40% by dry weight of arabinose units.

Embodiment 172 is the method of any one of embodiments 143-171, wherein the arabinoxylan comprises about 5% to about 25% by dry weight of arabinose units.

Embodiment 173 is the method of any one of embodiments 143-171, wherein the arabinoxylan comprises about 5% to about 15% by dry weight of arabinose units.

Embodiment 174 is the method of any one of embodiments 143-171, wherein the arabinoxylan comprises about 10% to about 20% by dry weight of arabinose units.

Embodiment 175 is the method of any one of embodiments 143-171, wherein the arabinoxylan comprises about 15% to about 25% by dry weight of arabinose units.

Embodiment 176 is the method of any one of embodiments 143-172, wherein the arabinoxylan comprises about 5% to about 7% by dry weight of arabinose units.

Embodiment 177 is the method of any one of embodiments 143-171, wherein the arabinoxylan comprises about 18% to about 20% by dry weight of arabinose units.

Embodiment 178 is the method of any one of embodiments 143-145 or 147-177, wherein the arabinoxylan comprises about 60% to about 85% by dry weight of xylose units.

Embodiment 179 is the method of any one of embodiments 143-178, wherein the arabinoxylan comprises about 60% to about 70% by dry weight of xylose units.

Embodiment 180 is the method of any one of embodiments 143-178, wherein the arabinoxylan comprises about 70% to about 80% by dry weight of xylose units.

Embodiment 181 is the method of any one of embodiments 143-178, wherein the arabinoxylan comprises about 75% to about 85% by dry weight of xylose units.

Embodiment 182 is the method of any one of embodiments 143-178, wherein the arabinoxylan comprises about 62% to about 66% by dry weight of xylose units.

Embodiment 183 is the method of any one of embodiments 143-178, wherein the arabinoxylan comprises about 78% to about 82% by dry weight of xylose units.

Embodiment 184 is the method of any one of embodiments 143-146 or 148-183, wherein the arabinoxylan comprises about 8% to about 15% by dry weight of glucose units.

Embodiment 185 is the method of any one of embodiments 143-184, wherein the arabinoxylan comprises about 10% to about 15% by dry weight of glucose units.

Embodiment 186 is the method of any one of embodiments 143-184, wherein the arabinoxylan comprises about 9% to about 11% by dry weight of glucose units.

Embodiment 187 is the method of any one of embodiments 143-184, wherein the arabinoxylan comprises about 12% to about 14% by dry weight of glucose units.

Embodiment 188 is the method of any one of embodiments 143-147 or 149-187, wherein the arabinoxylan comprises about 2% to about 6% by dry weight of galactose units.

Embodiment 189 is the method of any one of embodiments 143-188, wherein the arabinoxylan comprises about 3% to about 5% by dry weight of galactose units.

Embodiment 190 is the method of any one of embodiments 143-148 or 150-189, wherein the arabinoxylan comprises less than about 1% by dry weight of mannose units.

Embodiment 191 is the method of any one of embodiments 143-190, wherein the arabinoxylan comprises less than about 0.5% by dry weight of mannose units.

Embodiment 192 is the method of any one of embodiments 143-149 or 151-191, wherein the arabinoxylan comprises arabinose units and xylose units, and a molar ratio of the arabinose units and xylose units is about 0.05 to about 0.65.

Embodiment 193 is the method of any one of embodiments 143-192, wherein the arabinoxylan comprises arabinose units and xylose units, and a molar ratio of the arabinose units and xylose units is about 0.05 to about 0.35.

Embodiment 194 is the method of any one of embodiments 143-193, wherein the arabinoxylan comprises arabinose units and xylose units, and a molar ratio of the arabinose units and xylose units is about 0.05 to about 0.15.

Embodiment 195 is the method of any one of embodiments 143-193, wherein the arabinoxylan comprises arabinose units and xylose units, and a molar ratio of the arabinose units and xylose units is about 0.15 to about 0.25.

Embodiment 196 is the method of any one of embodiments 143-193, wherein the arabinoxylan comprises arabinose units and xylose units, and a molar ratio of the arabinose units and xylose units is about 0.25 to about 0.35.

Embodiment 197 is the method of any one of embodiments 143-194, wherein the arabinoxylan comprises arabinose units and xylose units, and a molar ratio of the arabinose units and xylose units is about 0.06 to about 0.10.

Embodiment 198 is the method of any one of embodiments 143-193, wherein the arabinoxylan comprises arabinose units and xylose units, and a molar ratio of the arabinose units and xylose units is about 0.28 to about 0.32.

Embodiment 199 is the method of any one of embodiments 143-150 or 152-198, wherein the arabinoxylan comprises glucose units and xylose units, and a molar ratio of the glucose units and xylose units is about 0.10 to about 0.25.

Embodiment 200 is the method of any one of embodiments 143-199, wherein the arabinoxylan comprises glucose units and xylose units, and a molar ratio of the glucose units and xylose units is about 0.15 to about 0.25.

Embodiment 201 is the method of any one of embodiments 143-200, wherein the arabinoxylan comprises glucose units and xylose units, and a molar ratio of the glucose units and xylose units is about 0.10 to about 0.20.

Embodiment 202 is the method of any one of embodiments 143-200, wherein the arabinoxylan comprises glucose units and xylose units, and a molar ratio of the glucose units and xylose units is about 0.11 to about 0.15.

Embodiment 203 is the method of any one of embodiments 143-200, wherein the arabinoxylan comprises glucose units and xylose units, and a molar ratio of the glucose units and xylose units is about 0.18 to about 0.22.

Embodiment 204 is the method of any one of embodiments 143-203, wherein the composition comprises less than about 1% by dry weight of carbohydrate polymers other than arabinoxylan.

Embodiment 205 is the method of any one of embodiments 143-204, wherein the composition comprises less than about 0.5% by dry weight of carbohydrate polymers other than arabinoxylan.

Embodiment 206 is the method of any one of embodiments 143-205, wherein the composition comprises about 0.5% to about 5% by dry weight of protein.

Embodiment 207 is the method of any one of embodiments 143-206, wherein the composition comprises about 1% to about 4% by dry weight of protein.

Embodiment 208 is the method of any one of embodiments 143-206, wherein the composition comprises about 0.8% to about 1.2% by dry weight of protein.

Embodiment 209 is the method of any one of embodiments 143-207, wherein the composition comprises about 3.6% to about 4% by dry weight of protein.

Embodiment 210 is the method of any one of embodiments 143-209, wherein the composition comprises about 0.5% to about 6% by dry weight of ash.

Embodiment 211 is the method of any one of embodiments 143-210, wherein the composition comprises about 1% to about 5% by dry weight of ash.

Embodiment 212 is the method of any one of embodiments 143-211, wherein the composition comprises about 1% to about 3% by dry weight of ash.

Embodiment 213 is the method of any one of embodiments 143-210, wherein the composition comprises about 0.8% to about 1.2% by dry weight of ash.

Embodiment 214 is the method of any one of embodiments 143-210, wherein the composition comprises about 4.5% to about 4.9% by dry weight of ash.

Embodiment 215 is the method of any one of embodiments 135-214, wherein the arabinoxylan has a molecular weight ($M_w$) of about 3100-8400 Da.

Embodiment 216 is the composition of any one of embodiments 143 or 145-215, wherein the arabinoxylan has a molecular weight of at least 4800 Da.

Embodiment 217 is the method of any one of embodiments 143-216, wherein the composition has a molecular weight ($M_w$) of about 5500-6000 Da.

Embodiment 218 is the method of any one of embodiments 143-217, wherein the composition has a molecular weight ($M_w$) of about 5500-5700 Da.

Embodiment 219 is the method of any one of embodiments 143-218, wherein the composition has a molecular weight ($M_w$) of about 5600-5800 Da.

Embodiment 220 is the method of any one of embodiments 143-219, wherein the composition has a molecular weight ($M_n$) of about 3000-3500 Da.

Embodiment 221 is the method of any one of embodiments 143-220, wherein the composition has a molecular weight ($M_n$) of about 3200-3400 Da.

Embodiment 222 is the method of any one of embodiments 152-154 or 156-221, wherein the one or more polyphenols comprise units selected from the group consisting of ferulic acid, gallic acid, 4-hydroxybenzoic acid, coumaric acid, syringic acid, sinapic acid, rosemarinic acid, vanillin, and combinations thereof.

Embodiment 223 is the method of any one of embodiments 152-154 or 156-22, wherein the composition comprises about 0.001% to about 0.005% by dry weight of ferulic acid units.

Embodiment 224 is the method of any one of embodiments 152-154 or 156-223, wherein the composition comprises about 0.001% to about 0.003% by dry weight of ferulic acid units.

Embodiment 225 is the method of any one of embodiments 152-154 or 156-224, wherein the composition comprises about 0.01% to about 0.05% by dry weight of gallic acid units.

Embodiment 226 is the method of any one of embodiments 152-154 or 156-225, wherein the composition comprises about 0.01% to about 0.03% by dry weight of gallic acid units.

Embodiment 227 is the method of any one of embodiments 152-154 or 156-226, wherein the composition comprises about 1% to about 2% by dry weight of 4-hydroxybenzoic acid units.

Embodiment 228 is the method of any one of embodiments 152-154 or 156-227, wherein the composition comprises about 1.0% to about 1.5% by dry weight of 4-hydroxybenzoic acid units.

Embodiment 229 is the method of any one of embodiments 152-154 or 156-228, wherein the composition comprises about 0.01% to about 0.05% by dry weight of coumaric acid units.

Embodiment 230 is the method of any one of embodiments 152-154 or 156-229, wherein the composition comprises about 0.01% to about 0.03% by dry weight of coumaric acid units.

Embodiment 231 is the method of any one of embodiments 152-154 or 156-230, wherein the composition comprises about 0.05% to about 0.1% by dry weight of syringic acid units.

Embodiment 232 is the method of any one of embodiments 152-154 or 156-231, wherein the composition comprises about 0.05% to about 0.07% by dry weight of syringic acid units.

Embodiment 233 is the method of any one of embodiments 152-154 or 156-232, wherein the composition comprises about 0.1% to about 0.5% by dry weight of synapic acid units.

Embodiment 234 is the method of any one of embodiments 152-154 or 156-233, wherein the composition comprises about 0.3% to about 0.5% by dry weight of synapic acid units.

Embodiment 235 is the method of any one of embodiments 152-154 or 156-234, wherein the composition comprises about 0.05% to about 0.3% by dry weight of rosemarinic acid units.

Embodiment 236 is the method of any one of embodiments 152-154 or 156-235, wherein the composition comprises about 0.1% to about 0.2% by dry weight of rosemarinic acid units.

Embodiment 237 is the method of any one of embodiments 152-154 or 156-236, wherein the composition comprises about 0.001% to about 0.01% by dry weight of vanillin units.

Embodiment 238 is the method of any one of embodiments 152-154 or 156-237, wherein the composition comprises about 0.004% to about 0.006% by dry weight of vanillin units.

Embodiment 239 is the method of any one of embodiments 143-238, wherein the composition is light brown.

Embodiment 240 is the method of any one of embodiments 143-239, wherein the composition has an antioxidant level of about 25000 to about 50000 µmol TE/100 g.

Embodiment 241 is the method of any one of embodiments 143-240, wherein the composition has an antioxidant level of about 25000 to about 35000 µmol TE/100 g.

Embodiment 242 is the method of any one of embodiments 143-241, wherein the composition comprises epigallocatechin gallate.

Embodiment 243 is a composition prepared by the method of any one of embodiments 128-242.

Embodiment 244 is a food product comprising a composition prepared by the method of any one of embodiments 128-242.

Embodiment 245 is a dietary supplement comprising a composition prepared by the method of any one of embodiments 128-242.

Embodiment 246 is a pharmaceutical composition comprising a composition prepared by the method of any one of embodiments 128-242.

Embodiment 247 is the food product of embodiment 243, the dietary supplement of embodiment 244, or the pharmaceutical composition of embodiment 245, wherein the composition prepared by the method of any one of embodiments 128-242 is present in an amount of at least 7 g per serving.

Embodiment 248 is the food product of embodiment 243, the dietary supplement of embodiment 244, or the pharmaceutical composition of embodiment 245, wherein the composition prepared by the method of any one of embodiments 128-242 is present in an amount of at least 10 g per serving.

Embodiment 249 is the food product of embodiment 243, the dietary supplement of embodiment 244, or the pharmaceutical composition of embodiment 245, wherein the composition prepared by the method of any one of embodiments 128-242 is present in an amount of at least 12 g per serving.

Embodiment 250 is the food product of embodiment 243, the dietary supplement of embodiment 244, or the pharmaceutical composition of embodiment 245, wherein the composition prepared by the method of any one of embodiments 128-242 is present in an amount of at least 14 g per serving.

Embodiment 251 is use of a composition prepared by the method of any one of embodiments 128-242 in a food product.

Embodiment 252 is use of a composition prepared by the method of any one of embodiments 128-242 in a pharmaceutical composition.

Embodiment 253 is use of a composition prepared by the method of any one of embodiments 128-242 in a dietary supplement.

Embodiment 255 is the use of any one of embodiments 251-253, wherein the composition prepared by the method of any one of embodiments 128-242 is present in an amount of at least 7 g per serving.

Embodiment 256 is the use of any one of embodiments 251-253, wherein the composition prepared by the method of any one of embodiments 128-242 is present in an amount of at least 10 g per serving.

Embodiment 257 is the use of any one of embodiments 251-253, wherein the composition prepared by the method of any one of embodiments 128-242 is present in an amount of at least 12 g per serving.

Embodiment 258 is the use of any one of embodiments 251-253, wherein the composition prepared by the method of any one of embodiments 128-242 is present in an amount of at least 14 g per serving.

EXAMPLES

Example 1

Wheat straw was treated using steam for a given temperature and time (activation step; see, e.g., U.S. Patent Application Publication No. 2018/0119188, herein incorporated by reference in its entirety), rendering the crude arabinoxylan water soluble.

The material was water extracted, and the liquid unprocessed arabinoxylan was removed via vacuum filtration to form a first soluble extract.

The first soluble extract was treated with a minimum amount of carbon (0.1% w/w) to remove compounds that can foul downstream membranes (e.g., soluble lignin and protein) but in such a way as to minimize AX yield losses by avoiding AX (with attached polyphenol groups) from adsorbing onto carbon.

The resulting arabinoxylan was then treated using nanofiltration to remove degradation compounds and impurities, such as salts and plant based inorganics. The membrane size was chosen to preserve AX yield (e.g., minimize the amount of AX that is filtered out with the impurities). This step also removed water and concentrated the AX prior to either evaporation to a syrup or drying to a powder.

Relatively pure AX (e.g., greater than about 90%) including polyphenols and color was then evaporated to a concentrated syrup or dried to a powder.

Example 2

Table 1 shows exemplary arabinoxylan compositions prepared by the process of Example 1. The exemplary compositions had an antioxidant level of about 29000 µmol TE/100 g.

TABLE 1

| | Exemplary Composition 1 | Exemplary Composition 2 |
|---|---|---|
| Composition (percent by dry weight of composition) | | |
| AX | 89 | 92 |
| Other NSP | 0 | 0 |

TABLE 1-continued

|  | Exemplary Composition 1 | Exemplary Composition 2 |
|---|---|---|
| Monomers | 4 | 1 |
| Protein | 1 | 3.8 |
| Ash | 1 | 4.7 |
| AX Composition (percent by dry weight of AX) | | |
| Arabinose | 6 | 19 |
| Xylose | 80 | 64 |
| Glucose | 10 | 13 |
| Galactose | 4 | 4 |
| Mannose | 0 | 0 |
| A:X ratio | 0.08 | 0.30 |
| Gluc:X ratio | 0.13 | 0.20 |
| Molecular weight | | |
|  | 5600 ($M_w$) | 5800 ($M_w$) |
|  |  | 3300 ($M_n$) |
| Polyphenol units (percent by dry weight of composition) | | |
| Ferulic | # | 0.002 |
| Gallic | # | 0.014 |
| 4-Hydroxybenzoic | # | 1.325 |
| Coumaric | # | 0.016 |
| Syringic | # | 0.061 |
| Sinapic | # | 0.391 |
| Rosemarinic | # | 0.114 |
| Vanillin | # | 0.005 |
| Total polyphenols | 3-11 | 1.928 |
| Color | | |
|  | light brown | light brown |

: Not Determined

Example 3

Wheat straw is treated with steam at about 110° C. to about 150° C. (e.g., about 130° C.) for about 5 minutes to about 30 minutes (e.g., about 15 minutes) at a pressure of about 10 psi to about 20 psi (e.g., about 15 psi) in a pre-activation step. The ratio of steam to wheat straw is about 0.1 to about 1.0 (e.g., about 0.1 to about 0.8, about 0.1 to about 0.5, about 0.1 to about 0.3, about 0.3 to about 1, about 0.5 to about 1, about 0.8 to about 1, about 0.3 to about 0.5, about 0.3 to about 0.8, or about 0.5 to about 0.8). The straw is then treated with steam at about 200° C. to about 240° C. (e.g., about 222° C.) for about 5 minutes to about 20 minutes (e.g., about 10 minutes) at a pressure of about 300 psi to about 350 psi (e.g., about 305 to about 335 psi). The ratio of steam to wheat straw is about 0.1 to about 2.0 (e.g., about 0.1 to about 1.5, about 0.1 to about 1.0, about 0.1 to about 0.5, about 0.5 to about 2.0, about 1.0 to about 2.0, about 1.5 to about 2.0, about 0.5 to about 1.5, about 0.5 to about 1.0, or about 1.0 to about 1.5).

The material is extracted with water at a temperature of about 25° C. to about 95° C. (e.g., about 25° C. to about 75° C., about 25° C. to about 50° C., about 50° C. to about 95° C., about 75° C. to about 95° C., about 25° C. to about 50° C., or about 25° C. to about 75° C.), and the arabinoxylan solution is removed via vacuum filtration.

Example 4

An unprocessed arabinoxylan (e.g., the unprocessed arabinoxylan of Example 3) is treated with about 0.05% to about 0.15% (e.g., 0.1% w/w) of activated carbon to remove compounds that can foul downstream membranes (e.g., soluble lignin and protein) but in such a way as to minimize AX yield losses by avoiding AX (with attached polyphenol groups) from adsorbing onto carbon.

The resulting composition is then treated using nanofiltration to remove degradation compounds and impurities, such as salts and plant based inorganics. The membrane size is chosen to preserve AX yield (e.g., minimize the amount of AX that is filtered out with the impurities). This step also removes water and concentrates the AX prior to either evaporation to a syrup or drying to a powder.

Relatively pure AX (e.g., greater than about 90%) including polyphenols and color is then evaporated to a concentrated syrup or dried to a powder.

Some properties of the prepared AX are shown in Tables 2 and 3.

TABLE 2

| Property | Composition according to Example 4 |
|---|---|
| Colour | brown |
| Antioxidant level (umol TE/100 g) | 25000-35000 |

TABLE 3

| | Composition according to Example 4 |
|---|---|
| Composition (percent by dry weight of composition) | |
| AX | 88-95 |
| Other NSP | 0-1 |
| Monomers | 0-5 |
| Protein | 0.5-6 |
| Ash | 0.5-6 |
| AX Composition (percent by dry weight of AX) | |
| Arabinose | 5-25 |
| Xylose | 60-85 |
| Glucose | 5-20 |
| Galactose | 2-6 |
| Mannose | 0-1 |
| A:X ratio | 0.05-0.35 |
| Gluc:X ratio | 0.10-0.25 |
| Molecular weight | |
|  | 5500-6000 ($M_w$) |
|  | 3000-3500 ($M_n$) |
| Polyphenol units (percent by dry weight of composition) | |
| Ferulic | 0.0005-0.005 |
| Gallic | 0.005-0.02 |
| 4-Hydroxybenzoic | 0.5-2 |
| Coumaric | 0.005-0.025 |
| Syringic | 0.01-0.1 |
| Sinapic | 0.2-0.6 |
| Rosemarinic | 0.05-0.3 |
| Vanillin | 0.001-0.01 |
| Total polyphenols | 1-12 |

Example 5

A high molecular weight arabinoxylan preparation is obtained from a commercial provider. The high molecular weight arabinoxylan preparation (which can have polyphenols attached and a higher molecular weight, e.g., higher than about 20 kDa (e.g., about 30 to about 300 kDa) and can have an alkaline pH (e.g., about 9 to about 14)) is treated with alkaline conditions, either in the presence or absence of an oxidizing agent and additives that can improve the performance of the oxidizing agent and elevated temperature. In some cases, temperature is between 60° C. and 200° C. (e.g., about 90° C.) for a period of 30 minutes to 8 hours (e.g., about 2 to 4 hours). In general, the higher the temperature, the lower a time is used. Typically, temperatures above 100° C. are not used, as they generally include a pressurized system which is more complicated and expensive. The resulting arabinoxylan has a molecular weight ($M_w$) of about 5500 to about 6000 Da.

Example 6

The arabinoxylan made in Example 5 is combined with a first soluble extract (e.g., the first soluble extract of Example 1). The combined arabinoxylan is treated with activated carbon and nanofiltration, for example, as in Example 4.

Example 7

The arabinoxylan made in Example 5 is treated with activated carbon and nanofiltration as described in Example 4.

Example 8

A Randomized, Placebo-Controlled, Crossover Study to Investigate the Effect of Arabinoxylan on Gastrointestinal Tolerance In Generally Healthy Adults This study was performed as a randomized, placebo-controlled, crossover trial with one screening visit (Visit 1; Week −1) and 3 test periods [Test Period 1 (Visits 2 and 3; Weeks 0 to 3), Test Period 2 (Visits 4 and 5; Weeks 5 to 8), and Test Period 3 (Visits 6 and 7; Weeks 10 to 13)] separated by minimum 2-week washout periods. Subjects consumed 11.6 g maltodextrin/day (placebo), 5.8 g maltodextrin/day and 7.25 g of Exemplary Composition 2 (Table 1)/day (providing 6.37 g arabinoxylan fiber/day), or 14.5 g of Exemplary Composition 2 (Table 1)/day (providing 12.74 g arabinoxylan fiber/day) for 3 weeks. Gastrointestinal (GI) symptoms were evaluated with multiple outcome measures collected from the Gastrointestinal Tolerability Questionnaire (GITQ), which was completed during the 7 days prior to the start of any intervention (baseline, Week 0) and prior to the end of each 3-week test period.

Subjects were men and women, 21 to 65 years of age (inclusive), each with a body mass index (BMI) of 18.5-35.0 kg/m² (inclusive) and regular bowel movements (by self-report).

Study Product
a. Placebo: 11.6 g maltodextrin/day
b. Active 1: 5.8 g maltodextrin/day and 7.25 g Exemplary Composition 2/day, which delivers 6.37 g arabinoxylan fiber/day
c. Active 2: 14.5 g Exemplary Composition 2/day, which delivers 12.74 g arabinoxylan fiber/day Subjects were instructed to consume study product daily for 3 weeks. Subjects were dispensed opaque sachets containing study products and were instructed to mix the components of each sachet thoroughly with 16 oz of water and to consume the entire beverage, then rinse the beverage container with some water and consume the additional water to be sure the entire study product was consumed. Consumption of the study product was completed within 10 minutes to 1 hour each time. Study product was consumed twice a day, once in the morning and once in the evening, with or without food.

Primary Outcome

Area under the curve (AUC) of the GITQ composite score was measured daily during the three test periods.

Analysis Population

Two sample populations were analyzed: Modified intent-to-treat (mITT) and per protocol (PP). The mITT population (n=44) included all randomized subjects that completed the appropriate questionnaires/study procedures. The PP (n=36) population is a subset of the mITT population, whereby subjects were excluded due to early termination/withdrawal of consent (n=3), failure to replicate diet (n=3), non-compliance (n=1), excessive body weight change during trial duration unrelated to study product (n=1), and flu with concomitant medication use during treatment period (n=1).

Statistical Analysis Approach

The AUC for the component GI tolerance score over the treatment period, restricted to 21 days, was calculated using the trapezoidal approximation:

$$\tfrac{1}{2}\Sigma(\text{day}_n - \text{day}_{n-1}) * (\text{score}_n + \text{score}_{n-1})$$

Two subjects had a period of 20 days. Due to nonlinearity of residuals, the AUC was ranked and modeled with a linear mixed model with a random intercept for subject nested within sequence. The backwards elimination approach was used to select a final adjusted model considering the following fixed effects: sequence, period, and prior treatment.

Results

There were no statistically significant differences (P>0.05) in the AUC of the GITQ composite score (Tables 4 and 5).

TABLE 4

AUC for GITQ Composite Score for the mITT Population

| Product | Unadjusted median (range) n = 42-44 | Model derived estimate (95% CI)[2] n = 42-44 | P value[1] vs placebo | P value[1] vs. 7.25 g Exemplary Composition 2 |
|---|---|---|---|---|
| Placebo | 10.00 (0.00, 94.00) | 60.89 (49.60, 72.18) | | 0.880 |
| 14.5 g Exemplary Composition 2 | 14.50 (0.00, 96.50) | 67.15 (55.98, 78.32) | 0.170 | |
| 7.25 g Exemplary Composition 2 | 11.75 (0.00, 157.50) | 67.83 (56.66, 79.00) | 0.130 | |

[1]Final adjusted model considered sequence, period, baseline, and prior product. Rank-based transformation was used.
[2]Model was rank-based; model derived estimate reflects the rank of the GITQ composite score.

Abbreviations: AX, arabinoxylan; CI, confidence interval; n, sample size; SD, standard deviation; SEM, standard error of the mean

TABLE 5

AUC for GITQ Composite Score for the PP Population

| Product | Unadjusted median (range) n = 36 | Model derived estimate (95% CI)[2] n = 36 | P value[1] vs placebo | P value[1] vs. 7.25 g Exemplary Composition 2 |
|---|---|---|---|---|
| Placebo | 11.00 (0.00, 94.00) | 62.63 (50.12, 75.14) | | 0.750 |
| 14.5 g Exemplary Composition 2 | 15.00 (0.00, 96.50) | 69.53 (57.01, 82.05) | 0.190 | |
| 7.25 g Exemplary Composition 2 | 12.75 (0.00, 157.50) | 67.86 (55.35, 80.38) | 0.320 | |

[1]Final adjusted model considered sequence, period, baseline, and prior product. Rank-based transformation was used.
[2]Model was rank-based; model derived estimate reflects the rank of the GITQ composite score.
Abbreviations: AX, arabinoxylan; CI, confidence interval; n, sample size; SD, standard deviation; SEM, standard error of the mean Summary Compared to placebo, daily consumption of 7.25 g and 14.5 g Exemplary Composition 2 (providing 6.37 g and 12.74 g arabinoxylan fiber, respectively) for 3 weeks did not affect GI tolerance.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising:
   about 80% to about 99% by dry weight of arabinoxylan, wherein the arabinoxylan has a molecular weight ($M_w$) of about 5500 Da to about 8400 Da.

2. A composition comprising:
   about 80% to about 95% by dry weight of arabinoxylan;
   about 4% to about 20% by dry weight of carbohydrate polymers other than arabinoxylan, sugar monomers, protein, and ash; and
   about 1% to about 14% by dry weight of one or more polyphenols.

3. The composition of claim 2, wherein the arabinoxylan comprises one or more of the following: about 5% to about 40% by dry weight of arabinose units; about 60% to about 85% by dry weight of xylose units; about 8% to about 15% by dry weight of glucose units; about 2% to about 6% by dry weight of galactose units; less than about 1% by dry weight of mannose units; arabinose units and xylose units, wherein a molar ratio of the arabinose units and xylose units is about 0.05 to about 0.65; or glucose units and xylose units, wherein a molar ratio of the glucose units and xylose units is about 0.10 to about 0.25.

4. The composition of claim 2, wherein the composition comprises one or more of the following: less than about 1% by dry weight of carbohydrate polymers other than arabinoxylan; about 0.5% to about 5% by dry weight of protein; or about 0.5% to about 6% by dry weight of ash.

5. The composition of claim 2, wherein the arabinoxylan has a molecular weight ($M_w$) of about 3100-8400 Da.

6. The composition of claim 1, wherein the composition has a molecular weight ($M_w$) of about 5500-6000 Da.

7. The composition of claim 2, wherein the one or more polyphenols comprise units selected from the group consisting of ferulic acid, gallic acid, 4-hydroxybenzoic acid, coumaric acid, syringic acid, sinapic acid, rosemarinic acid, vanillin, and combinations thereof.

8. The composition of claim 1, wherein the composition has an antioxidant level of about 25000 to about 50000 μmol TE/100 g.

9. A composition comprising:
   about 88% to about 90% by dry weight of arabinoxylan, wherein the arabinoxylan comprises:
   about 5% to about 7% by dry weight of arabinose units;
   about 78% to about 82% by dry weight of xylose units;
   about 9% to about 11% by dry weight of glucose units;
   about 3% to about 4% by dry weight of galactose units;
   about 4% to about 6% of carbohydrate polymers that are not arabinoxylan, sugar monomers, protein, ash, or a combination thereof; and
   about 3% to about 11% by dry weight of one or more polyphenols,
   wherein the molecular weight ($M_w$) of the composition is about 5400 to about 5800 Da.

10. A composition comprising:
    about 90% to about 94% by dry weight of arabinoxylan, wherein the arabinoxylan comprises:
    about 17% to about 21% by dry weight of arabinose units;
    about 62% to about 66% by dry weight of xylose units;
    about 12% to about 14% by dry weight of glucose units;
    about 3% to about 4% by dry weight of galactose units;
    about 8% to about 11% of carbohydrate polymers that are not arabinoxylan, sugar monomers, protein, ash, or a combination thereof; and
    about 1% to about 3% by dry weight of one or more polyphenols,
    wherein the molecular weight ($M_w$) of the composition is about 5600 to about 6000 Da.

11. A food product comprising the composition of claim 2.

12. A dietary supplement comprising the composition of claim 2.

13. A pharmaceutical composition comprising the composition of claim 2.

14. A method of preparing a composition, said method comprising:
    providing a lignocellulosic biomass;
    combining the lignocellulosic biomass with water;
    activating the lignocellulosic biomass and water using conditions comprising a first temperature and a first pressure to form a first activated cellulose stream;
    washing the first activated cellulose stream to form a washed first activated cellulose stream and a first soluble extract, wherein the first soluble extract comprises arabinoxylan; and processing the first soluble extract to form a composition comprising about 80% to about 99% by dry weight of arabinoxylan, wherein the arabinoxylan has a molecular weight ($M_w$) of about 5500 Da to about 8400 Da.

15. The method of claim 14, wherein processing comprises one or more of treating with carbon, nanofiltering, or a combination thereof.

16. The method of claim 14, wherein processing comprises, sequentially, treating with carbon and nanofiltering to form the composition.

17. The method of claim 14, wherein processing does not comprise treating with carbon.

18. The method of claim 14, further comprising, prior to processing, adding a reduced-mass arabinoxylan to the first soluble extract.

19. The method of claim 14, wherein the composition comprises:
   about 80% to about 95% by dry weight of arabinoxylan;
   about 4% to about 20% by dry weight of carbohydrate polymers other than arabinoxylan, sugar monomers, protein, ash, or a combination thereof; and
   about 1% to about 14% by dry weight of one or more polyphenols.

20. The method of claim 19, wherein the arabinoxylan comprises one or more of the following: about 5% to about 40% by dry weight of arabinose units; about 60% to about 85% by dry weight of xylose units; about 8% to about 15% by dry weight of glucose units; about 2% to about 6% by dry weight of galactose units; less than about 1% by dry weight of mannose units; arabinose units and xylose units, wherein a molar ratio of the arabinose units and xylose units is about 0.05 to about 0.65; or glucose units and xylose units, wherein a molar ratio of the glucose units and xylose units is about 0.10 to about 0.25.

21. The method of claim 19, wherein the composition comprises one or more of the following: less than about 1% by dry weight of carbohydrate polymers other than arabinoxylan; about 0.5% to about 5% by dry weight of protein; or about 0.5% to about 6% by dry weight of ash.

* * * * *

UNITED STATES PATENT AND TRADEMARK OFFICE
CERTIFICATE OF CORRECTION

PATENT NO. : 12,263,184 B2
APPLICATION NO. : 17/609684
DATED : April 1, 2025
INVENTOR(S) : Andrew Richard, Dennis D'Agostino and Ana-Teodora Ivanov-Dragut Page 1 of 1

It is certified that error appears in the above-identified patent and that said Letters Patent is hereby corrected as shown below:

In the Claims

Column 46, Line 18, in Claim 7: delete "rosemarinic" and insert --rosmarinic--, therefor.

Signed and Sealed this
Seventeenth Day of June, 2025

Coke Morgan Stewart
*Acting Director of the United States Patent and Trademark Office*